US012213978B2

(12) United States Patent
Apcher et al.

(10) Patent No.: US 12,213,978 B2
(45) Date of Patent: Feb. 4, 2025

(54) MADRASIN-DERIVATIVE COMPOUNDS, COMPOSITION AND USES THEREOF FOR TREATING CANCER

(71) Applicants: INSTITUT GUSTAVE ROUSSY, Villejuif (FR); INSERM (INSTITUT NATIONAL DE LA SANTÉ ET DE LA RECHERCHE MÉDICALE), Paris (FR); CENTRE NATIONAL DE LA RECHERCHE SCIENTIFIQUE, Paris (FR); UNIVERSITE PARIS-SACLAY, Gif-sur-Yvette (FR)

(72) Inventors: Sébastien Apcher, Franconville (FR); Mouad Alami, Bussy Saint Georges (FR); Romain Darrigrand, Sauveterre de Béarn (FR); Samir Messaoudi, Ballainvilliers (FR); Valérie Salgues, Nogent sur Marne (FR); Zafiarisoa Dolor Renko, Les Ulis (FR); Expedite Yen-Pon, Plaine des Palmistes (FR)

(73) Assignees: INSERM (INSTITUT NATIONAL DE LA SANTÉ ET DE LA RECHERCHE MÉDICALE), Paris (FR); CENTRE NATIONAL DE LA RECHERCHE SCIENTIFIQUE, Paris (FR); INSTITUT GUSTAVE ROUSSY, Villejuif (FR); UNIVERSITE PARIS-SACLAY, Gif-sur-Yvette (FR)

( * ) Notice: Subject to any disclaimer, the term of this patent is extended or adjusted under 35 U.S.C. 154(b) by 793 days.

(21) Appl. No.: 17/293,506

(22) PCT Filed: Nov. 15, 2019

(86) PCT No.: PCT/EP2019/081516
§ 371 (c)(1),
(2) Date: May 13, 2021

(87) PCT Pub. No.: WO2020/099650
PCT Pub. Date: May 22, 2020

(65) Prior Publication Data
US 2022/0047597 A1 Feb. 17, 2022

(30) Foreign Application Priority Data
Nov. 15, 2018 (EP) .................................... 18306499

(51) Int. Cl.
A61K 31/517 (2006.01)
A61K 31/5377 (2006.01)
A61K 31/661 (2006.01)
A61K 31/7064 (2006.01)
A61K 45/06 (2006.01)
A61P 35/00 (2006.01)

(52) U.S. Cl.
CPC ........ *A61K 31/517* (2013.01); *A61K 31/5377* (2013.01); *A61K 31/661* (2013.01); *A61K 31/7064* (2013.01); *A61K 45/06* (2013.01); *A61P 35/00* (2018.01)

(58) Field of Classification Search
None
See application file for complete search history.

(56) References Cited

FOREIGN PATENT DOCUMENTS

WO  WO-2011085129 A2 *  7/2011  ............. A61K 31/47
WO  WO 2017/165495      9/2017

OTHER PUBLICATIONS

Zhang et al., "The impact of both platinum-based chemotherapy and EGFR-TKIs on overall survival of patients with advanced non-small cell lung cancer", 2014, Chinese Journal of Cancer, 33, pp. 105-114 (Year: 2014).*
Meyskens et al., "Cancer Prevention: Obstacles, Challenges, and the Road Ahead", 2016, J Natl Cancer Inst, pp. 1-8 (Year: 2016).*
Darrigranda, R. et al. "Spliceosome is a druggable target for epitope-based Immunotherapies" Internet Citation, [Online] Apr. 1, 2018 (Apr. 1, 2018), XP002791331, pp. 1-2, retrieved from the internet on May 15, 2019: URL:https://www.universite-paris-saclay.fr/sites/default/files/livret-symposium-drugdiscoverynewtherapeutics.pdf>.

(Continued)

*Primary Examiner* — Jeffrey H Murray
*Assistant Examiner* — Madeline E Braun
(74) *Attorney, Agent, or Firm* — SALIWANCHIK, LLOYD & EISENSCHENK

(57) ABSTRACT

The present invention relates to the fields of medicine and in particular cancer treatment. The invention more specifically relates to new compounds which are typically for use as a medicament. In particular, the invention relates to the use of these new compounds for increasing the presentation, typically the production and presentation, of Pioneer Translation Products (PTPs)-derived antigens by cells, in particular cancer cells, or changing the immunopeptidome, in a subject, and inducing or stimulating an immune response in the subject. The present disclosure also relates to uses of such compounds, in particular to prepare a pharmaceutical composition and/or to allow or improve the efficiency of a therapy in a subject in need thereof. The invention also discloses methods for treating a disease, in particular cancer, for preventing or treating cancer metastasis and/or cancer recurrence, in a subject. The present invention in addition provides kits suitable for preparing a composition according to the present invention and/or for implementing the herein described methods.

Figure 1:
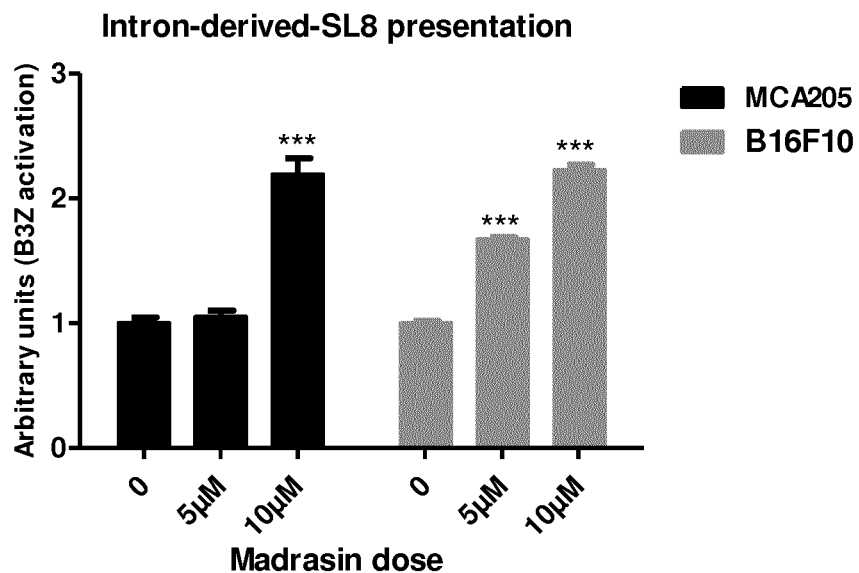
Figure 1:
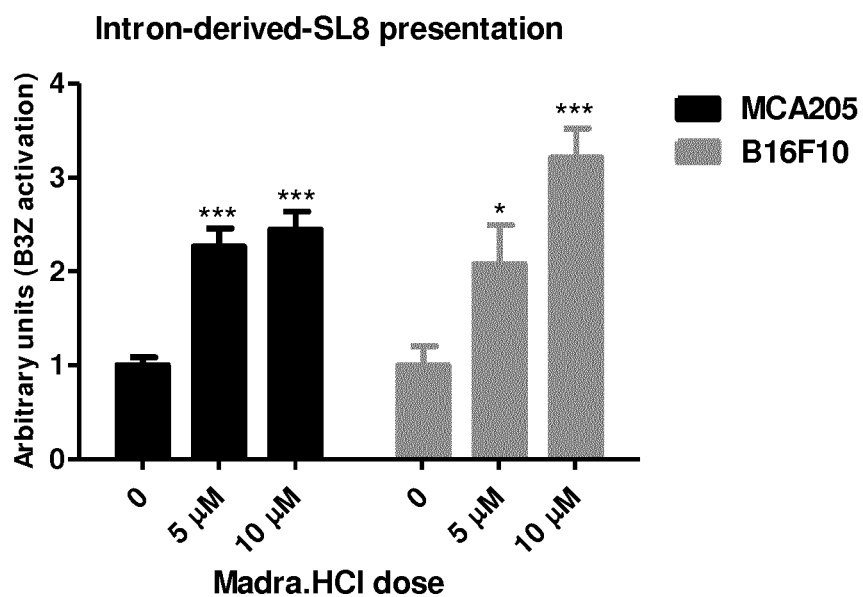
Figure 1:
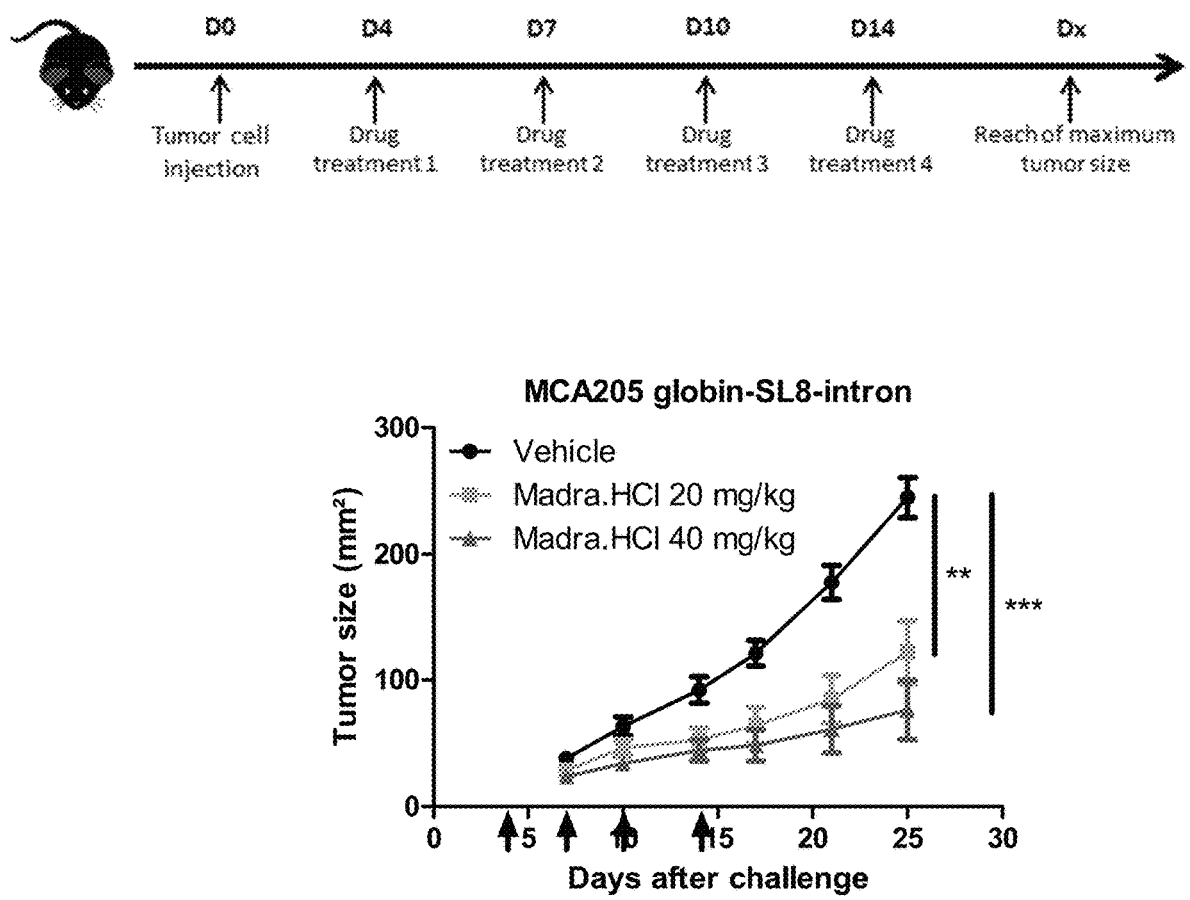
Figure 1:
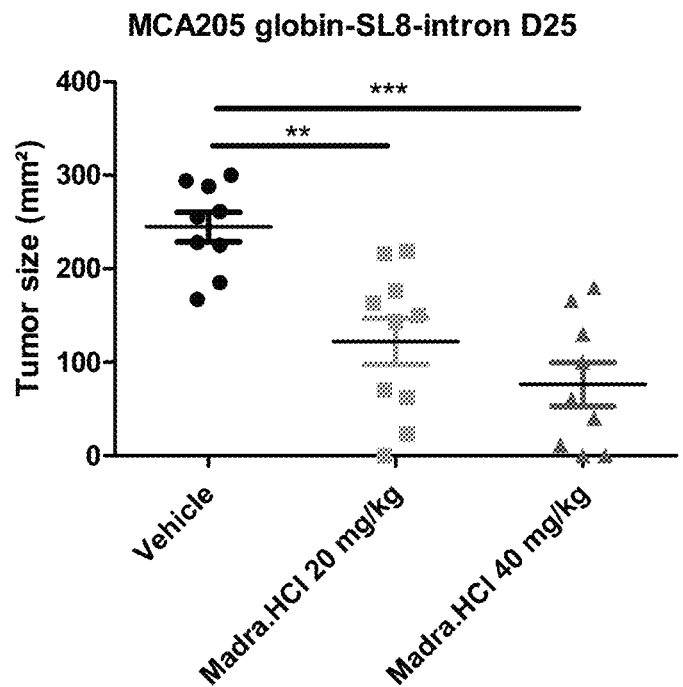
Figure 1:
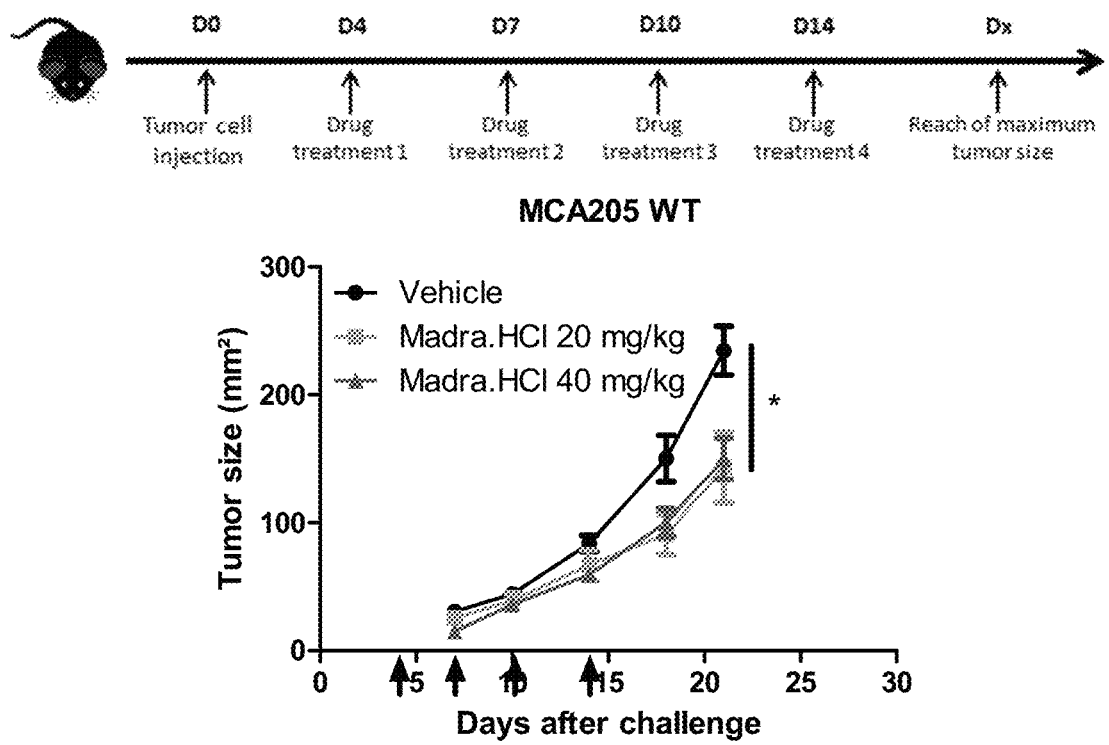
Figure 1:
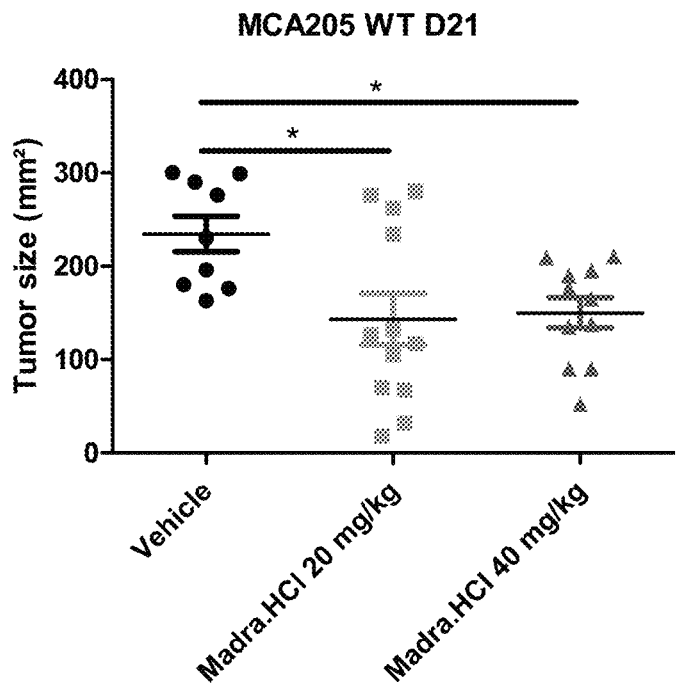
Figure 1:
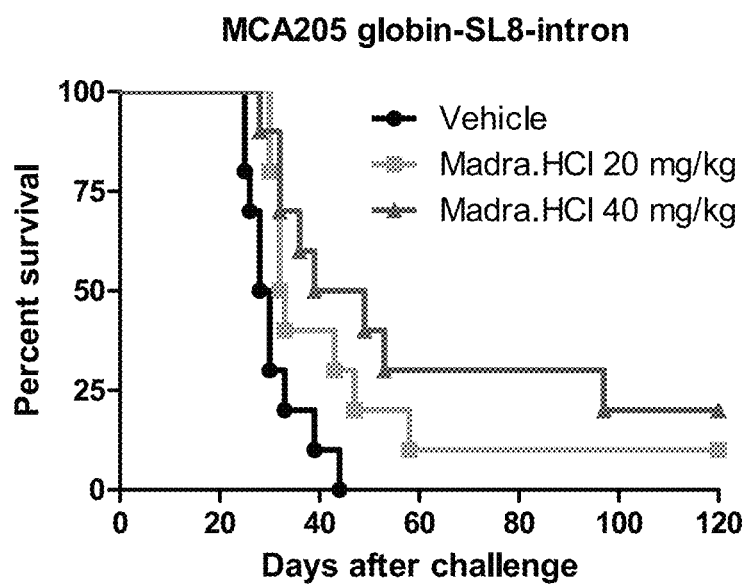
Figure 1:
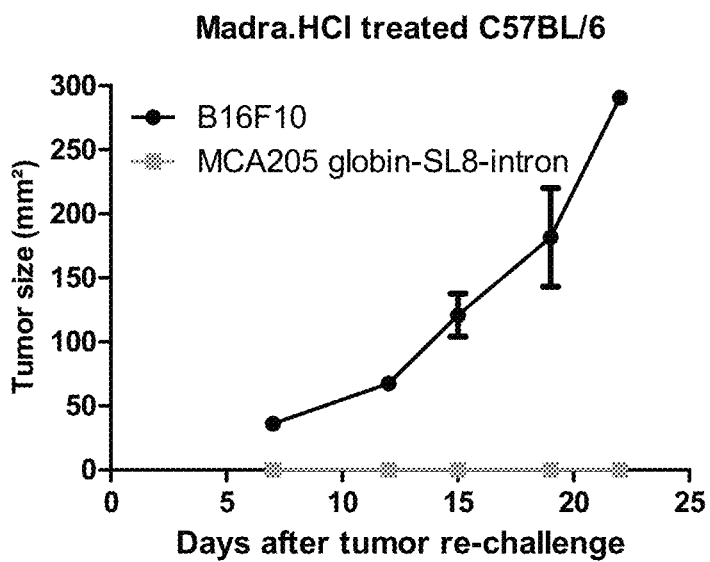

15 Claims, 22 Drawing Sheets
Specification includes a Sequence Listing.

(56) References Cited

OTHER PUBLICATIONS

Pawellek, A. et al. "Identification of Small Molecule Inhibitors of Pre-mRNA Splicing" *The Journal of Biological Chemistry*, Dec. 12, 2014, pp. 34683-34698, vol. 289, No. 50.
Salton, M. et al. "Small molecule modulators of pre-mRNA splicing in cancer therapy" *Trends Mol Med*. Jan. 2016, pp. 1-18, vol. 22, No. 1.
Written Opinion in International Application No. PCT/EP2019/081516, Apr. 3, 2020, pp. 1-9.

\* cited by examiner

C

D

E

F

G

H

A

B

A

B

C

D

A

B

A

B

C

D

A

B

C

D

A

B

C

A

B

Madrasin's derivatives including compound 32:

Madrasin's derivatives 41, 42, 43, 46, 49, 50, 54 and 57

MADRASIN-DERIVATIVE COMPOUNDS, COMPOSITION AND USES THEREOF FOR TREATING CANCER

CROSS-REFERENCE TO RELATED APPLICATION

This application is the U.S. national stage application of International Patent Application No. PCT/EP2019/081516, filed Nov. 15, 2019.

STATEMENT REGARDING SEQUENCE LISTING

The Sequence Listing for this application is labeled "Seq-List.txt" which was created on Apr. 14, 2021 and is 418 bytes. The entire content of the sequence listing is incorporated herein by reference in its entirety.

FIELD OF THE INVENTION

The present disclosure generally relates to the fields of medicine and in particular cancer treatment. The invention more specifically relates to new compounds which are derivatives of Madrasin and are each typically for use as a medicament. In particular, the invention relates to the use of these new compounds for increasing the presentation, typically the production and presentation, of (antigenic) peptides, preferably Pioneer Translation Products (PTPs)-derived antigens by cells, in particular by cancer cells, or changing the immunopeptidome, in a subject, and inducing or stimulating an immune response in the subject. The immune response is typically directed against a tumor antigen, more generally against the cancerous tumour the subject is suffering of.

The present disclosure also relates to uses of such compounds, in particular to prepare a pharmaceutical composition and/or to allow or improve the efficiency of a therapy, in particular of a cancer therapy, in a subject in need thereof. Each of the compounds of the invention can indeed be advantageously used, in combination with at least one distinct anticancer agent, typically a chemotherapeutic drug, and/or with radiotherapy, for treating cancer, for preventing or treating cancer metastasis and/or for preventing cancer recurrence in a subject.

The invention also discloses methods for treating a disease, in particular cancer, for preventing or treating cancer metastasis and/or cancer recurrence, in a subject. The present invention in addition provides kits suitable for preparing a composition according to the present invention and/or for implementing the herein described methods.

BACKGROUND OF THE INVENTION

All nucleated cells present antigenic peptides (APs) at their surface trough the class I major histocompatibility complex (MHC-I) pathway. APs are 8 to 10 amino acids long and reflect the inherent cellular activity (Caron et al.). Because their presentation guides the surveillance of potentially dangerous elements by immune cells, mainly cytotoxic CD8$^+$ T cells (CTL) and CD4$^+$ T helper cells, APs are the targets of therapeutic anti-cancer vaccines currently developed. Despite promising, clinical trials results with therapeutic vaccines targeting tumor-associated antigens (TAA) haven't met their expectations. The main failures have been associated to immunosuppressive mechanisms and to a suboptimal choice of antigens (Mellman et al.; Burg et al.).

One of the important events that drive tumors immunoselection, and that is correlated to poor prognosis, is the loss or the downregulation of MHC class I antigenic presentation by tumor cells (Watson et al.; Liu et al.). These last can escape CTL and natural killer cells recognition due to defects in components of the MHC class I pathway (Leone et al.). Along with the overall decrease of MHC class I antigenic presentation, the nature of antigens presented at the cell surface, called the MHCI class I immunopeptidome (MIP), is of critical importance for immune recognition. In cancer where a specific TAA is identified and targeted with immunotherapy such as Her/neu in breast cancer or CEA in colon cancer, the loss of this TAA expression at the tumor cell surface leads to immune evasion (Lee et al.; Kmieciak et al.). To counteract that, current strategies aims at enlarging the range of targeted cancer peptide and restoring MHC antigenic presentation.

In order to understand the dynamic of the MIP, one could focus on the source of APs for the MHC class I presentation pathway. Endogenous APs were first thought to strictly come from the degradation of senescent proteins. However, models suggesting alternative sources have challenged this notion. In 1996, the group of J. Yewdell introduces the concept of the Defective ribosomal products (DRIPs) (Yewdell et al.), initially described as rapidly degraded products due to their unstable conformation. More recently, inventors have explored that concept from a different perspective showing that the major source of APs derive from a pioneer translation event that occurs before introns are spliced out and that is independent of the translation event of full-length proteins (Apcher et al.). Produced non-canonical peptides can therefore be derived from intronic sequence, 3' or 5' UTR regions as well as alternative reading frames. These polypeptides are described as Pioneer Translation Products (PTPs). The discovery of PTPs suggests the existence of a complex translational nuclear mechanism that partly aims at shaping the MIP by generating relevant and suitable polypeptides for the MHC class I pathway. Moreover, PTPs seems to play a role in the dynamic of cancer development. When inoculated in mice, it has been shown that cancer cells presenting PTPs-derived antigens at their surface can be recognized by specific T-cells leading to tumor growth reduction. Moreover, purified PTPs containing a model epitope efficiently promote anti-cancer immune response when injected as a peptide vaccine in mice (Duvallet et al.).

Precursor-mRNA (pre-mRNA) splicing is catalyzed in the nucleus by the spliceosome, a conserved and dynamic multi-protein complex composed of five small nuclear RNAs (snRNAs) U1, U2, U4, U5 and U6 that are complexes with over 200 proteins. A growing number of studies report that the deregulation of the spliceosome complex entails aberrant splicing patterns in many cancers contributing to abnormal tumor cell proliferation and progression. Since 2011, recurrent spliceosome mutations have been reported in several cancers, including myelomonocytic leukemia, myeloid leukemia, chronic lymphocytic leukemia, breast cancers or multiple myeloma.

Darrigrand et al. (Drug Discovery and new Therapeutics, First international symposium of Paris-Saclay University, April 2018) teaches that spliceosome is a druggable target for epitope-based immunotherapies. WO2017/165495 describes PIM kinase inhibitors in combination with RNA splicing modulators/inhibitors for treatment of cancers. Salton et al. disclose the use of small molecule Pre-mRNA Splicing Modulators in cancer therapy. In recent years several microbial natural products and their synthetic analogues have been reported to inhibit the spliceosome, including the pladienolides B and D, spliceostatin A, FR901464, E7107, the Isoginkgetin and the madrasin. Inventors tested the potential effect as modulators of the antigenic presentation of some of each.

Here, they show that Madrasin and some of the derivatives they generated can be used as positive immunomodulators against cancer. They looked at the antigenic presentation of a PTPs-derived antigen model expressed in mouse cancer cell lines and observed that in vitro treatment with madrasin and the herein described different derivatives increases the presentation of the antigens. In addition, they showed that in vivo treatment with the madrasin hydrochloride (also herein identified as "Madra.HCl", as EYP34 or as the compound of formula I) dissolved in water of sarcoma-bearing mice slows down tumor growth in an immune-dependent manner. In order to ameliorate its effect, they tested different madrasin derivatives that are soluble or not in water and observed that some were more potent inhibitors of mouse sarcoma growth than madrasin itself. Since in immunodeficient Nu/Nu mice, the natural product and the derivative have no effect on tumor growth they conclude that their effects are dependent on the immune response. Those results indicate that PTPs-derived antigenic presentation can be modulated by treatments and that splicing inhibition can boost the anti-cancer response. Inventors herein describe another mechanism of action of splicing inhibitors that can be used as positive immunomodulators to potentiate the anti-tumoral immune response.

Inventors now herein describe new compounds for use in the treatment of diseases, in particular in the treatment of cancer, in the prevention of cancer metastasis and/or in the prevention of cancer recurrence in a subject.

SUMMARY OF THE INVENTION

Inventors produced and herein describe for the first time the formulas of the following particular compounds derived from Madrasin:

Madrasin hydrochloride (also herein identified as "Madr.HCl", as "EYP34" or as "compound of formula I")

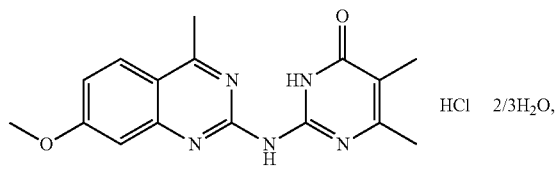

HCl 2/3H$_2$O, 5,6-Dimethyl-2-((4-methyl-7-(2-morpholinoethoxy)quinazolin-2-yl)amino)pyrimidin-4(3H)-one (also herein identified as "EYP201", "compound 6" or as "compound of formula II")

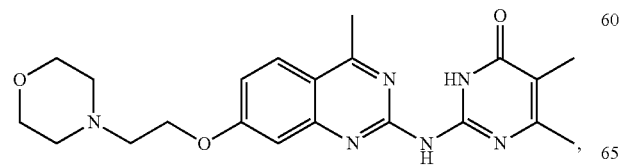

Sodium 2-((4,5-dimethyl-6-oxo-1,6-dihydropyrimidin-2-yl)amino)-4-methylquinazolin-7-yl phosphate (also herein identified as "EYP59", "compound 7" or as "compound of formula III")

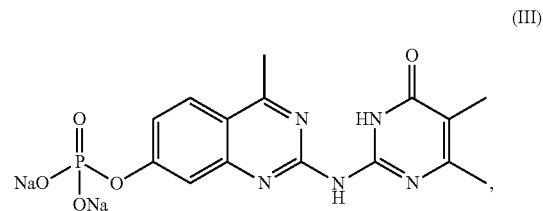

wherein "Na" represents a "sodium" and the radical of formula —ONa designates a "sodium hydroxide", N-(2-Methoxypyrimidin-5-yl)quinazolin-2-amine (also herein identified as "EYP281", "compound 32" or as "compound of formula IV")

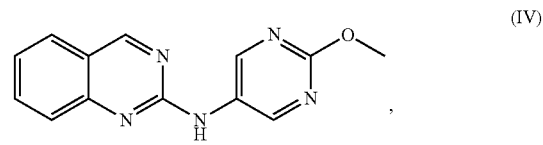

N-(1H-Indol-3-yl)-7-methoxy-4-methylquinazolin-2-amine (also herein identified as "EYP165", "compound 57" or as "compound of formula V")

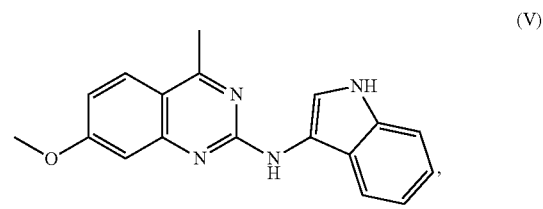 [SMILES: COc1ccc2c(C)nc(Nc3c[nH]c4ccccc34)nc2c1]

((1S,2S,4R,5S,6S)-5-Acetoxy-7,8-diacetyl-4-((2-((4,5-dimethyl-6-oxo-1,6-dihydropyrimidin-2-yl)amino)-7-methoxy-4-methylquinazolin-8-yl)thio)-3,7λ3,8λ3-trioxabicyclo[4.2.0]octan-2-yl)methyl acetate (also herein identified as "EYP86", "compound 10" or as "compound of formula VI")

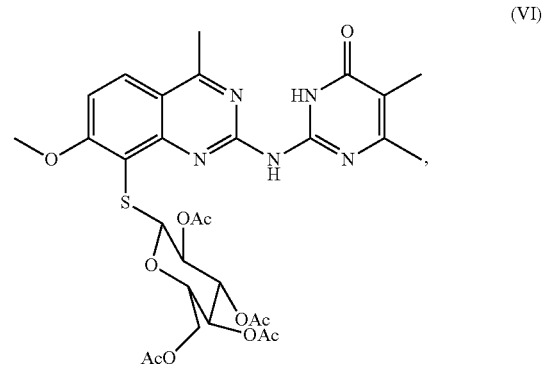

wherein the radical of formula —OAc designates a "Acetoxy group" of the structure CH3-C(=O)—O—, 7-Methoxy-4-methyl-N-(3,4,5-trimethoxyphenyl)quinazolin-2-amine (also herein identified as "EYP188", "compound 42" or as "compound of formula VII")

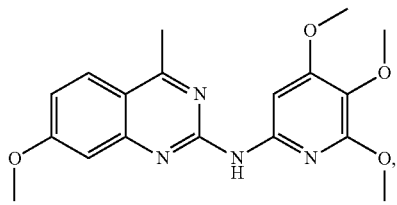

(VII)

7-Methoxy-N-(6-methoxypyridin-3-yl)-4-methylquinazolin-2-amine (also herein identified as "EYP174", "compound 41" or as "compound of formula VIII")

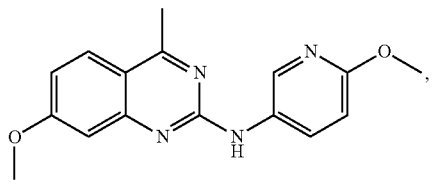

(VIII)

N2-(7-Methoxy-4-methylquinazolin-2-yl)-N4-methylpyrimidine-2,4-diamine (also herein identified as "EYP181", "compound 49" or as "compound of formula IX")

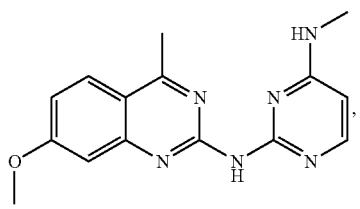

(IX)

7-Methoxy-N-(4-methoxypyrimidin-2-yl)-4-methylquinazolin-2-amine (also herein identified as "EYP179", "compound 50" or as "compound of formula X")

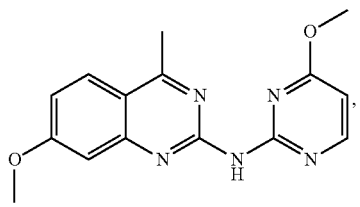

(X)

and

7-Methoxy-N-(2-methoxypyrimidin-4-yl)-4-methylquinazolin-2-amine (also herein identified as "EYP190", "compound 54" or as "compound of formula XI")

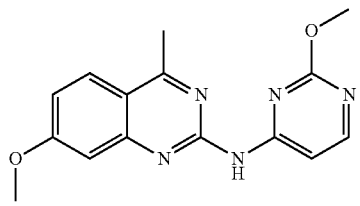

(XI)

Each of these compounds, as well as any combination thereof, is herein described for use as a medicament.

Any of these compounds, as well as a pharmaceutically acceptable salt thereof, can advantageously be used as a medicament.

In a preferred aspect herein described, any of the herein above described compounds of formula (I) to (XI), or a pharmaceutically acceptable salt thereof, or any combination thereof, is for use in the treatment of a disease, in particular is for use in the treatment of a cancer, for use in the prevention of cancer metastasis and/or for use in the prevention of cancer recurrence, in a subject.

Further described is the in vivo, in vitro or ex vivo use of a compound of a formula selected from formula (I) to (XI) for inducing or increasing the presentation, typically the production and presentation, of (antigenic) peptides, preferably Pioneer Translation Products (PTPs)-derived antigens by cells, in particular by cancer cells, or changing the immunopeptidome, in a subject.

The compound of a formula selected from formula (I) to (XI) allows the physician to prevent or control, preferably decrease, cancer cell proliferation by stimulating the subject's immune system. It is in addition advantageously capable of increasing the effectiveness of other cancer treatments. Inventors herein demonstrate that this compound is in addition capable of reducing the risk of metastasis and/or cancer recurrence.

Also herein described is a composition comprising such a compound of a formula selected from formula (I) to (XI) and a pharmaceutically acceptable carrier, preferably together with at least one distinct anticancer agent to be used simultaneously, separately or sequentially. Such a composition is typically for use for treating a disease, in particular for treating a cancer, for preventing cancer metastasis and/or for preventing cancer recurrence, in a subject.

Also herein described is a method for treating a disease, in particular for treating cancer, in a subject, comprising a step of administering a compound, typically a compound of a formula selected from formula (I) to (XI), or a composition as herein described to the subject.

A kit is also described which comprises a compound of a formula selected from formula (I) to (XI) and preferably at least one distinct anticancer agent in distinct containers, as well as uses thereof, in particular to prepare a composition as herein described.

DETAILED DESCRIPTION OF THE INVENTION

Inventors generated Madrasin derivatives which are described for the first time in the context of the present invention and are more precisely identified below as compounds of formulas (I) to (XI):

Madrasin hydrochloride (also herein identified as "Madr.HCl", as "EYP34" or as "compound of formula I")

(I)

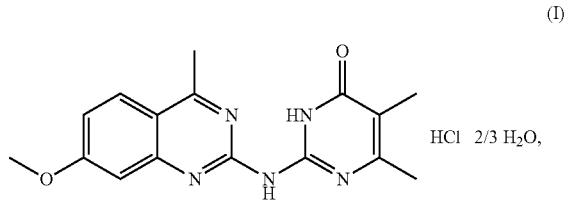

HCl 2/3 H₂O, 5,6-Dimethyl-2-((4-methyl-7-(2-morpholinoethoxy)qui-nazolin-2-yl)amino)pyrimidin-4(3H)-one (also herein identified as "EYP201", "compound 6" or as "compound of formula II")

(II)

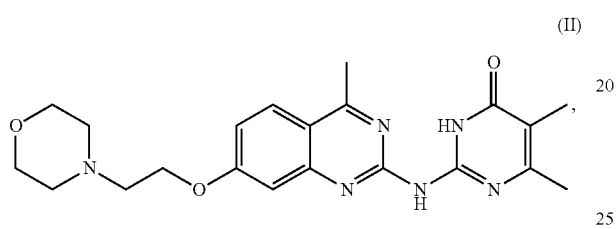

Sodium 2-((4,5-dimethyl-6-oxo-1,6-dihydropyrimidin-2-yl)amino)-4-methylquinazolin-7-yl phosphate (also herein identified as "EYP59", "compound 7" or as "compound of formula III")

(III)

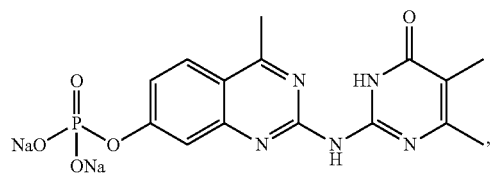

wherein "Na" represents a "sodium" and the radical of formula —ONa designates a "sodium hydroxide"

N-(2-Methoxypyrimidin-5-yl)quinazolin-2-amine (also herein identified as "EYP281", "compound 32" or as "compound of formula IV")

(IV)

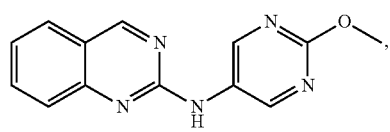

N-(1H-Indol-3-yl)-7-methoxy-4-methylquinazolin-2-amine (also herein identified as "EYP165", "compound 57" or as "compound of formula V")

(V)

((1S,2S,4R,5S,6S)-5-Acetoxy-7,8-diacetyl-4-((2-((4,5-dimethyl-6-oxo-1,6-dihydropyrimidin-2-yl)amino)-7-methoxy-4-methylquinazolin-8-yl)thio)-3,7λ3,8λ3-tri-oxabicyclo[4.2.0]octan-2-yl)methyl acetate (also herein identified as "EYP86", "compound 10" or as "compound of formula VI")

(VI)

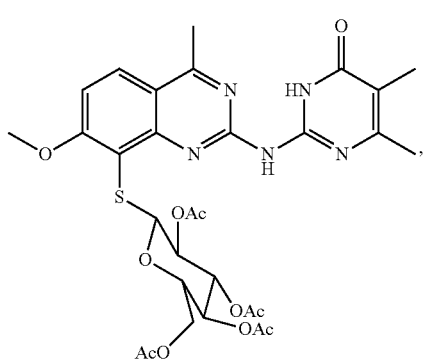

wherein the radical of formula —OAc designates a "Acetoxy group" of the structure CH3-C(=O)—O—, 7-Methoxy-4-methyl-N-(3,4,5-trimethoxyphenyl)qui-nazolin-2-amine (also herein identified as "EYP188", "compound 42" or as "compound of formula VII")

(VII)

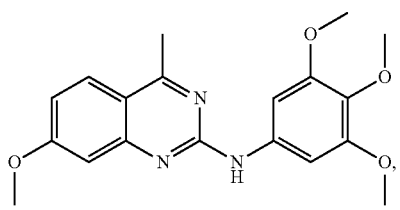

7-Methoxy-N-(6-methoxypyridin-3-yl)-4-methylqui-nazolin-2-amine (also herein identified as "EYP174", "compound 41" or as "compound of formula VIII")

(VIII)

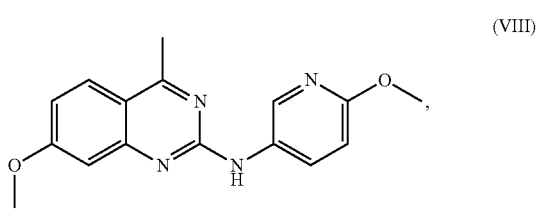 [SMILES: COc1ccc2c(C)nc(Nc3ccc(OC)nc3)nc2c1]

N2-(7-Methoxy-4-methylquinazolin-2-yl)-N4-methylpyrimidine-2,4-diamine (also herein identified as "EYP181", "compound 49" or as "compound of formula IX")

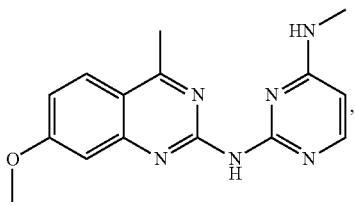

7-Methoxy-N-(4-methoxypyrimidin-2-yl)-4-methylquinazolin-2-amine (also herein identified as "EYP179", "compound 50" or as "compound of formula X")

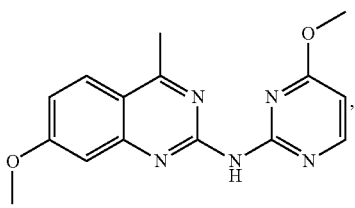

and
7-Methoxy-N-(2-methoxypyrimidin-4-yl)-4-methylquinazolin-2-amine (also herein identified as "EYP190", "compound 54" or as "compound of formula XI")

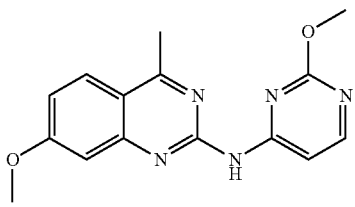

In a particular aspect, inventors herein describe a compound of formula (A):

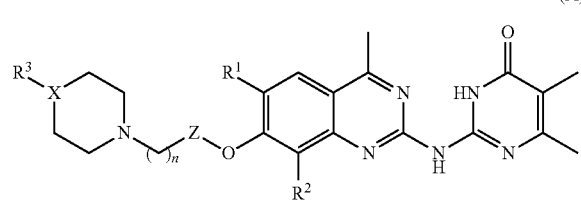

wherein:
$R^1$ and $R^2$ are independently selected from H, $CH_4$ (Methyl) and Cl (Chlorine),
$R^3$ is H, $CH_4$ (Methyl), $C_2H_6$ (Ethyl), n-Propyl, $N(CH_2)_4$ or $N(CH_2)_5$,
Z is $CH_2$ or C=O,
n is 1, 2 or 3, and
X is O, N or CH.

In a particular and preferred aspect, the compound of formula (A) is the compound of formula II (also identified as "EYP201" or "compound 6").

In another particular aspect, inventors herein describe a compound of formula (B):

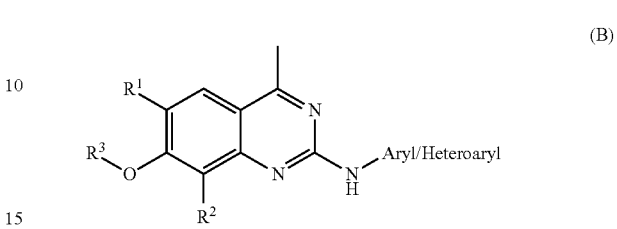

wherein:
$R^1$ and $R^2$ are independently selected from H, $CH_4$ (Methyl), Cl (Chlorine) and a thiosugar; and
$R^3$ is $P(O)(ONa)_2$ or wherein:
$R^4$ is H, $CH_4$ (Methyl), $C_2H_6$ (Ethyl), n-Propyl, $N(CH_2)_4$ or $N(CH_2)_5$,
Z is $CH_2$ or C=O,
n is 1, 2 or 3, and
X is O, N or CH.

The aryl group can be for example 3,4,5-trimethoxyphenyl; 2-chloro-3,4,5-trimethoxyphenyl; 3,5-trimethoxyphenyl; or 2-chloro-3,5-trimethoxyphenyl.

The heteroaryl group can be for example 3-indolyl; 2-indoyl; 2-imidazole; 2-benzimidazole; carbazole; N-methylpyrimidine; methoxypyrimidin-2-yl; methoxypyrimidin-4-yl; methoxypyridin-2-yl or methoxypyridin-4-yl.

In a particular aspect, the compound of formula (B) is selected from the compound of formula (III), the compound of formula (V), the compound of formula (VI), the compound of formula (VII), the compound of formula (VIII), the compound of formula (IX), the compound of formula (X) and the compound of formula (XI).

Any of the herein above described compound of formula (A) and (B) or (I) to (XI), as well as a pharmaceutically acceptable salt thereof, can advantageously be used as a medicament.

As used herein, the term "pharmaceutically acceptable" refers to compositions, compounds, salts and the like that are, within the scope of sound medical judgment, suitable for contact with the tissues of the subject, or which can be administered to the subject, without excessive toxicity or other complications commensurate with a reasonable benefit/risk ratio. For instance, pharmaceutically acceptable salts encompass sodium, potassium, chloride, ammonium, acetate salts and the like.

Inventors herein demonstrate that the compounds of formulas (A), (B) and (I) to (XI) can advantageously be used as positive immunomodulators, in particular against cancer.

Inventors looked at the antigenic presentation of a PTPs-derived antigen model expressed in mouse cancer cell lines and observed that their in vitro treatment with Madrasin and, more preferably a compound of a formula selected from formula (A) and (B) or (I) to (XI), increases the presentation of this antigen. In addition, they showed that in vivo treatment with the Madrasin dissolved in DMSO of sarcoma-bearing mice slows down tumor growth in an immune-dependent manner. In order to ameliorate its effect, they tested the herein described Madrasin derivatives that are soluble in water and surprisingly observed that they are far more potent inhibitors of cancer growth than Madrasin itself. Since in immunodeficient Nu/Nu mice, the natural product and the derivative have no effect on tumor growth they concluded that their effects are dependent on the immune response. Those results demonstrate that PTPs-derived antigenic presentation can be modulated and inventors provide new promising molecules for market development which can be used to boost in particular the anti-cancer response and treat cancer contrary to other derivatives of Madrasin.

In a preferred aspect herein described, the compound of a formula selected from formula (A) and (B) or (I) to (XI), in particular the compound of formula (I), (II), (III), (V), (V), (VI), (VII), (VIII), (IX), (X) or (XI) (also herein identified as the "compounds of interest"), is for use in the treatment of a disease, in particular of a cancer, for use in the prevention of cancer metastasis and/or for use in the prevention of cancer recurrence, in a subject.

In another preferred aspect herein described, the compound of a formula selected from formula (A) and (B) or (I) to (XI) is for use for stimulating an anti-cancer immune response in a subject in need thereof.

In a further preferred aspect, the compound of a formula selected from formula (A) and (B) or (I) to (XI) is for use for inducing or increasing the presentation, typically the production and presentation, of Pioneer Translation Products (PTPs)-derived antigens by cancer cells, or changing the immunopeptidome, in a subject.

The compounds of the invention can be obtained by methods well-known by the skilled artisan such as hemi-synthesis or total synthesis. Examples of methods for producing the compounds of interest are herein described in the experimental part and further illustrated on FIGS. 9 and 10. The compounds of formulas (A), (B) and (I) to (XI) are artificial products which cannot be found as such in nature.

The compound of formulas (A), (I) to (III) and (VI) can be typically prepared from Madrasin which has been described as a permeant inhibitor of pre-mRNA splicing. The compound of formula (IV), (V), (VII) to (XI) can be prepared by chemical synthesis by using conventional chemical reactions.

A further object of the invention is the use of a compound of a formula selected from formula (A) and (B) or (I) to (XI) (or a pharmaceutically acceptable salt thereof) for decreasing the resistance of a cancer or subject suffering of cancer with respect to a distinct anticancer agent, typically a distinct chemotherapeutic agent.

Also herein described is a compound of a formula selected from formula (A) and (B) or (I) to (XI), according to the invention (or a pharmaceutically acceptable salt thereof), or a composition comprising such a compound and a pharmaceutically acceptable carrier, for use, in combination with at least one distinct anticancer agent, typically a distinct chemotherapeutic drug, and/or with radiotherapy, for treating a disease, in particular for treating a cancer, for preventing cancer metastasis and/or for preventing cancer recurrence in a subject.

The term "subject" refers to any subject, preferably a mammal.

Examples of mammals include humans and non-human animals such as, without limitation, domesticated animals (e.g., cows, sheep, cats, dogs, and horses), non-human primates (such as monkeys), rabbits, and rodents (e.g., mice and rats). The treatment is preferably intended for a human being in need thereof, whatever its age or sex.

The term "subject" typically designates a patient, in particular a patient having a tumor. Unless otherwise specified in the present disclosure, the tumor is a cancerous or malignant tumor. In a particular aspect, the subject is a subject undergoing a treatment of cancer such as chemotherapy and/or radiotherapy, or a subject at risk, or suspected to be at risk, of developing a cancer.

The subject is, for example a human being suffering of a cancer and resistant to cancer treatment, typically to chemotherapy.

The subject may have been exposed to part of a complete conventional treatment protocol, for example to at least one cycle of the all treatment protocol, for example two cycles of the all treatment protocol.

The cancer or tumor may be any kind of cancer or neoplasia. The tumor is typically a solid tumor, in particular of epithelial, neuroectodermal or mesenchymal origin. The cancer is also typically selected from a carcinoma, sarcoma, lymphoma, germ cell tumor, blastoma, leukemia and multiple myeloma, preferably from a carcinoma, sarcoma, blastoma, lymphoma, leukemia and multiple myeloma. The cancer can be a metastatic cancer or not.

The cancer can for example be selected from, without being limited to, the group consisting of chronic myeloid leukemia, acute lymphoblastic leukemia, Philadelphia chromosome positive acute lymphoblastic leukemia (Ph$^+$ ALL), Hodgkin's disease, Hodgkin's or non-Hodgkin lymphoma, squamous cell carcinoma, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, brain cancer, central nervous system cancer, pancreatic cancer, glioblastoma multiforme, cervical cancer, stomach cancer, bladder cancer, malignant hepatoma, breast cancer, colon carcinoma, head and neck cancer, gastric cancer, germ cell tumor, pediatric sarcoma, rhabdomyosarcoma, Ewing's sarcoma, osteosarcoma, soft tissue sarcoma, sinonasal NK/T-cell lymphoma, myeloma, melanoma, multiple myeloma, acute myelogenous leukemia (AML), and chronic lymphocytic leukemia.

In a preferred embodiment, the cancer is selected from the group consisting of lung cancer, breast cancer, genitourinary cancer (such as prostate cancer, bladder cancer, testis cancer, uterine cervix cancer or ovaries cancer) and sarcoma (such as osteosarcoma or soft tissue sarcoma, including pediatric soft tissue sarcoma, neuroblastoma, myeloma and melanoma).

In a particular embodiment, the cancer is a sarcoma.

More preferably, the cancer is selected from melanoma, lung cancer (including non-small-cell lung carcinoma (or NSCLC) and small-cell lung carcinoma (or SCLC)) and breast cancer.

Even more preferably, the carcinoma is a melanoma or a lung cancer.

In an aspect, the cancer is a lung cancer, typically a small-cell lung cancer or a non-small cell lung cancer.

In another aspect, the cancer is a leukemia, typically an acute myelogenous leukemia (AML) or a chronic lymphocytic leukemia.

In a further aspect, the cancer is a colon cancer, typically a colon carcinoma. The cancer may also be a colorectal cancer.

In a further aspect, the cancer is a pediatric cancer typically a pediatric sarcoma, lymphoma, leukemia, neuroblastoma, brain cancer, or central nervous system cancer.

In a particular aspect herein described, the anticancer agent is selected from a chemotherapeutic agent, an immune checkpoint blocker and an anti-cancer vaccine (also herein identified as "cancer vaccine"). These agents are typically considered as "conventional" agents for treating cancer.

The chemotherapeutic agent is typically an agent selected for example from an antitumor/cytotoxic antibiotic, an alkylating agent, an antimetabolite, a topoisomerase inhibitor, a mitotic inhibitor, a platin based component, a specific kinase inhibitor, an hormone, a cytokine, an antiangiogenic agent, an antibody, a DNA methyltransferase inhibitor and a vascular disrupting agent.

The antitumor agent or cytotoxic antibiotic can for example be selected from an anthracycline (e.g. doxorubicin, daunorubicin, adriamycine, idarubicin, epirubicin, mitoxantrone, valrubicin), actinomycin, bleomycin, mitomycin C, plicamycin and hydroxyurea.

The alkylating agent can for example be selected from mechlorethamine, cyclophosphamide, melphalan, chlorambucil, ifosfamide, temozolomide busulfan, N-Nitroso-N-methylurea (MNU), carmustine (BCNU), lomustine (CCNU), semustine (MeCCNU), fotemustine, streptozotocin, dacarbazine, mitozolomide, thiotepa, mytomycin, diaziquone (AZQ), procarbazine, hexamethylmelamine and uramustine.

The antimetabolite can for example be selected from a pyrimidine analogue (e.g. a fluoropyrimidine analog, 5-fluorouracil (5-FU), floxuridine (FUDR), cytosine arabinoside (Cytarabine), Gemcitabine (Gemzar®), capecitabine); a purine analogue (e.g. azathioprine, mercaptopurine, thioguanine, fludarabine, pentostatin, cladribine, clofarabine); a folic acid analogue (e.g. methotrexate, folic acid, pemetrexed, aminopterin, raltitrexed, trimethoprim, pyrimethamine).

The topoisomerase inhibitor can for example be selected from camptothecin, irinotecan, topotecan, amsacrine, etoposide, etoposide phosphate and teniposide.

The mitotic inhibitor can for example be selected from a taxane [paclitaxel (PG-paclitaxel and DHA-paclitaxel) (Taxol®), docetaxel (Taxotère®), larotaxel, cabazitaxel, ortataxel, tesetaxel, or taxoprexin]; a spindle poison or a vinca alkaloid (e.g. vincristine, vinblastine, vinorelbine, vindesine or vinflunine); mebendazole; and colchicine.

The platin based component can for example be selected from platinum, cisplatin, carboplatin, nedaplatin, oxaliplatin, satraplatin and triplatin tetranitrate.

The specific kinase inhibitor can for example be selected from a BRAF kinase inhibitor such as vemurafenib; a MAPK inhibitor (such as dabrafenib); a MEK inhibitor (such as trametinib); and a tyrosine kinase inhibitor such as imatinib, gefitinib, erlotinib, sunitinib or carbozantinib.

Tamoxifen, an anti-aromatase, or an anti-estrogen drug can also typically be used in the context of hormonotherapy.

A cytokine usable in the context of an immunotherapy can be selected for example from IL-2 (Interleukine-2), IL-11 (Interleukine-11), IFN (Interferon) alpha (IFNa), and Granulocyte-macrophage colony-stimulating factor (GM-CSF).

The anti-angiogenic agent can be selected for example from bevacizumab, sorafenib, sunitinib, pazopanib and everolimus.

The antibody, in particular the monoclonal antibody (mAb) can be selected from a anti-CD20 antibody (anti-pan B-Cell antigen), anti-Her2/Neu (Human Epidermal Growth Factor Receptor-2/NEU) antibody; an antibody targeting cancer cell surface (such as rituximab and alemtuzumab); a antibody targeting growth factor (such as bevacizumab, cetuximab, panitumumab and trastuzumab); a agonistic antibody (such as anti-ICOS mAb, anti-OX40 mAb, anti-41BB mAb); and an immunoconjugate (such as 90Y-ibritumomab tiuxetan, 131I-tositumomab, or ado-trastuzumab emtansine).

A DNA methyltransferase inhibitor can for example be selected from 2'-deoxy-5-azacytidine (DAC), 5-azacytidine, 5-aza-2'-deoxycytidine, 1-[beta]-D-arabinofuranosyl-5-azacytosine and dihydro-5-azacytidine.

A vascular disrupting agent can for example be selected from a flavone acetic acid derivative, 5,6-dimethylxanthenone-4-acetic acid (DMXAA) and flavone acetic acid (FAA).

Other chemotherapeutic drugs include a proteasome inhibitor (such as bortezomib), a DNA strand break compound (such as tirapazamine), an inhibitor of both thioredoxin reductase and ribonucleotide reductase (such as xcytrin), and an enhancer of the Th1 immune response (such as thymalfasin).

In a preferred embodiment, the chemotherapeutic drug or agent is selected from an antitumor/cytotoxic antibiotic, an alkylating agent, an antimetabolite, a topoisomerase inhibitor, a mitotic inhibitor, a platin based component, a specific kinase inhibitor, an antiangiogenic agent, an antibody and a DNA methyltransferase inhibitor.

An immune checkpoint blocker is typically an antibody targeting an immune checkpoint. Such an immune checkpoint blocker can be advantageously selected from anti-CTLA4 (ipilimumab and Tremelimumab), anti-PD-1 (Nivolumab and Pembrolizumab), anti-PD-L1 (Atezolizumab, Durvalumab, and Avelumab), anti-PD-L2 and anti-Tim3.

The cancer vaccine can for example be selected from a vaccine composition comprising (antigenic) peptides, in particular PTPs; a Human papillomavirus (HPV) vaccine (such as Gardasil®, Gardasil9®, and Cervarix®); a vaccine stimulating an immune response to prostatic acid phosphatase (PAP) sipuleucel-T (Provenge®); an oncolytic virus; and talimogene laherparepvec (T-VEC or Imlygic®).

In another particular aspect, the ("conventional") cancer treatment is an irradiation (also herein identified as "radiotherapy"). The radiotherapy typically involves rays selected from X-rays ("XR"), gamma rays and/or UVC rays.

The treatment which can include several anticancer agents is selected by the cancerologist depending on the specific cancer to be prevented or treated.

A particular melanoma is a melanoma conventionally treated with ipilimumab, nivolumab, pembrolizumab, IFNα, dacarbazine, a BRAF inhibitor, dabrafenib, trametinib, sorafenib, temozolomide, electrochemotherapy, TNFalpha and/or fotemustine.

In a particular embodiment, the melanoma is a melanoma resistant to the previously described cytotoxic conventional therapies.

A particular breast cancer is a breast cancer conventionally treated with an anthracycline, a taxane, trastuzumab, an anti-PARP (Poly (ADP-ribose) polymerase), an anti-PI3K (Phosphoinositide 3-kinase), a mTOR (mammalian Target of Rapamycin) inhibitor, vinorelbine, gemcitabine, an antioestrogen, and/or an antiaromatase, before or after a surgical step to remove breast tumor, preferably before such a surgical step.

In a particular embodiment, the breast cancer is a breast cancer resistant to the previously described conventional therapies.

A particular lung cancer is a lung cancer conventionally treated with XR and either platine or permetrexed.

A particular early stage NSCLC is an NSCLC conventionally treated with paclitaxel, docetaxel gemcitabine, vinorelbine, etoposide, taxane, avastin [anti-VEGF (Vascular endothelial growth factor) antibody], erlotinib and/or gefitinib. In a particular embodiment, the lung cancer is resistant to conventional therapies.

A particular colon cancer, also known as a colorectal cancer or bowel cancer, is conventionally treated with an antimetabolite (5-FU, raltitrexed), a platin based component (oxaliplatin), a topoisomerase inhibitor (irinotecan), an antibody targeting growth factor (bevacizumab, cetuximab, panitumumab) after a surgical step to remove breast tumor.

The present disclosure further relates to the use of a compound of a formula selected from formula (A) and (B) or (I) to (XI) according to the invention (or a pharmaceutically acceptable salt thereof) to prepare a pharmaceutical composition or medicament, said composition being capable of treating a disease, in particular a cancer, or of improving the efficiency of a therapy, in a subject in need thereof by stimulating the subject's immune system.

In a particular aspect, the compound is selected from the compound of formula (A), (B), II, III, IV, V, VI and VII, and the cancer is a sarcoma.

In another particular aspect, the compound is selected from the compound of formula II, III, IV, V, VIII, IX, X and XI, and the carcinoma is a melanoma.

The compound of the invention can in particular be advantageously used, in combination with at least one distinct anti-cancer agent as described previously or any other therapeutically active compound, and/or with radiotherapy, for treating a disease, in particular for treating a cancer, for preventing cancer metastasis and/or for preventing cancer recurrence, in a subject.

Also herein described is thus a composition comprising, typically as a combined preparation, a compound of a formula selected from formula (A) and (B) or (I) to (XI) and a pharmaceutically acceptable carrier, preferably together with at least one distinct therapeutic agent, in particular anticancer agent, for simultaneous, separate or sequential use in the treatment of the disease, in particular of the cancer.

Herein described are also (i) a method for treating a disease, in particular a cancer, (ii) a method for increasing the sensitivity of a disease, in particular a cancer, to a therapeutic/anticancer agent, and (iii) a method for decreasing the resistance of a disease/cancer with respect to a therapeutic/anticancer agent, each of said methods comprising administering a subject in need thereof with an effective amount, typically a therapeutically effective amount, of at least one compound of a formula selected from formula (A) and (B) or (I) to (XI), or a pharmaceutical composition as defined above, preferably together with another therapeutic/anticancer agent classically used in the treatment of the disease/cancer as herein described (as a combined preparation).

In another particular aspect, said method further comprises administering an effective amount of another therapeutically active compound for treating a disease/cancer or for preventing or treating a disease/cancer treatment side effect.

As used herein, "treatment" or "treat" refers to therapeutic intervention in an attempt to alter the natural course of the subject being treated, and is typically performed for curative purpose. Desirable effects of treatment include, but are not limited to, preventing recurrence of disease, alleviation of symptoms, and diminishment of any direct or indirect pathological consequences of the disease, decreasing the rate of disease progression, amelioration or palliation of the disease state, and remission or improved prognosis. In preferred embodiments, compositions and methods of the invention are used to delay development of a cancer or to slow the progression of a cancer, typically of tumor growth.

Typically, the treatment will induce a therapeutic response of the immune system of the subject, typically $CD4^+$ and/or $CD8^+$ T cells response(s).

By inducing a T cell response is typically meant herein that a T cell response directed towards a certain antigen is elicited. Before said induction, said T cell response was not present, or below detection levels or not functional. By enhancing a T cell response is meant herein that the overall action of T cells directed towards a certain antigen is made higher and/or more efficient compared to the overall action of said T cells before said enhancement. For instance, after said enhancement more T cells directed towards said antigen may be generated. As a result, the action of the additionally generated T cells increases the overall action against said antigen. Alternatively, said enhancement may comprise the increment of the action of T cells directed towards said antigen. Said T cells may for instance react stronger and/or quicker with said antigen. Of course, the result of said enhancement may be generation of additional T cells together with increment of the action of said T cells. Alternatively, said enhancement may comprise generation of additional T cells, or increment of the action of T cells, only.

Another object herein described relates to a method of producing an immune response in a subject, typically against a specific target, preferably a tumor antigen or cancer/tumor cell or tissue, the method comprising injecting to said subject a compound of a formula selected from formula (A) and (B) or (I) to (XI) according to the invention or composition according to the invention comprising such a compound, typically in an effective amount.

The detection of a therapeutic immune response can be easily determined by the skilled person thanks to technologies such as ELISA, ELISPOT, delayed type hypersensitivity response, intracellular cytokine staining, and/or extracellular cytokine staining.

As used herein, "an effective amount or dose" or "a therapeutically effective amount or dose" refers to an amount of the compound of the invention which removes, slows down the disease, in particular the cancer, or reduces or delays one or several symptoms or disorders caused by or associated with said disease in the subject, or which induce a measurable immune response in the subject, who is preferably a human being. The effective amount, and more generally the dosage regimen, of the compound of the invention and pharmaceutical compositions thereof may be determined and adapted by the one skilled in the art. An effective dose can be determined by the use of conventional techniques and by observing results obtained under analogous circumstances. The therapeutically effective dose of the compound of the invention will vary depending on the disease to be treated, its gravity, the route of administration, any co-therapy involved, the patient's age, weight, general medical condition, medical history, etc.

Typically, the amount of the compound to be administrated to a patient may range from about 0.01 mg/kg to 500 mg/kg of body weight for a human patient. In a particular embodiment, the pharmaceutical composition according to the invention comprises 0.1 mg/kg to 100 mg/kg of the compound of the invention, for instance from 0.5 mg/kg to 10 mg/kg.

In a particular aspect, the compounds of interest of the invention can be administered to the subject by parenteral route, oral route, or intravenous (IV), intratumoral (IT) or intraperitoneal (IP) injection. The compound of the invention may be administered to the subject daily (one time a day) during several consecutive days, for example during 2 to 10 consecutive days, preferably from 3 to 6 consecutive days. Said treatment may be repeated during 1, 2, 3, 4, 5, 6 or 7 weeks, or every two or three weeks or every one, two or three months. Alternatively, several treatment cycles can be performed, optionally with a break period between two treatment cycles, for instance of 1, 2, 3, 4 or 5 weeks. Anyone of the herein described compounds of the invention can for example be administered as a single dose once a week, once every two weeks, or once a month. The treatment may be repeated one or several times per year.

Doses are administered at appropriate intervals which can be determined by the skilled person. The amount chosen will depend on multiple factors, including the route of administration, duration of administration, time of administration, the elimination rate of the selected compound having a formula selected from formula (A) and (B) or (I) to (XI), or of the various products used in combination with said compound, the age, weight and physical condition of the patient and his/her medical history, and any other information known in medicine.

The administration route can be performed by various routes. For example, it can be oral or parenteral.

It is typically performed by systemic injection, e.g., intravenous, intra-muscular, intra-peritoneal, intra-tumoral, sub-cutaneous, etc. The pharmaceutical composition is adapted for one or several of the above-mentioned routes. The pharmaceutical composition is preferably administered by injection or by intravenous infusion of suitable sterile solutions, or in the form of liquid or solid doses via the alimentary canal.

The pharmaceutical composition can be formulated as solutions in pharmaceutically compatible solvents or vehicles, or as pills, tablets, capsules, powders, suppositories, etc. that contain solid vehicles in a way known in the art, possibly through dosage forms or devices providing sustained and/or delayed release. For this type of formulation, an agent such as cellulose, lipids, carbonates or starches are used advantageously.

Agents or vehicles that can be used in the formulations (liquid and/or injectable and/or solid) are excipients or inert vehicles, i.e. pharmaceutically inactive and non-toxic vehicles.

Mention may be made, for example, of saline, physiological, isotonic and/or buffered solutions, compatible with pharmaceutical use and known to those skilled in the art. The compositions may contain one or more agents or vehicles chosen from dispersants, solubilizers, stabilizers, preservatives, etc.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations suitable for parenteral administration conveniently comprise a sterile oily or aqueous preparation of the active ingredient which is preferably isotonic with the blood of the recipient. Every such formulation can also contain other pharmaceutically compatible and non-toxic auxiliary agents, such as, e.g. stabilizers, antioxidants, binders, dyes, emulsifiers or flavouring substances.

The formulations of the present invention comprise an active ingredient, a compound having a formula selected from formula (A) and (B) or (I) to (XI) according to the invention (or a pharmaceutically acceptable salt thereof), in association with a pharmaceutically acceptable carrier and optionally with other active or therapeutic ingredients. The carrier must be "acceptable" in the sense of being compatible with the other ingredients of the formulations and not deleterious to the recipient thereof. Methods for the safe and effective administration of most of these anti-cancer agents are known to those skilled in the art. In addition, their administration is described in the standard literature.

Another object of the invention is a kit comprising at least one compound having a formula selected from formula (A) and (B) or (I) to (XI) according to the invention (or a pharmaceutically acceptable salt thereof), and preferably at least one distinct therapeutic agent, in particular anticancer agent, typically chemotherapeutic drug, in distinct containers. The kit can further comprise instructions for preparing a composition according to the invention, for carrying out anyone of the herein described method, for example for treating a disease, in particular a cancer, for preventing or treating cancer metastasis and/or for preventing or treating cancer recurrence, in a subject.

In a particular embodiment, the present invention relates to the use of a kit according to the invention to prepare a composition as herein described.

In another particular embodiment, the kit is suitable for implementing anyone of the herein described method, in particular a method for treating cancer, for preventing cancer metastasis and/or for preventing cancer recurrence in a subject.

Further aspects and advantages of the present invention will be disclosed in the following experimental section and figures which shall be considered as illustrative only.

LEGENDS TO THE FIGURES

FIGS. 1A and 1B: Madrasin and Madra.HCl treatment increase intron-derived antigen presentation in cancer cells.

B3Z specific T-cell activation in MCA205 sarcoma cells and B16F10 melanoma cells expressing the intron-derived SL8 antigen after treatment with 5 µM or 10 µM (A) Madrasin (B) Madra.HCl. Free SL8 peptide was added in each condition to ensure that T-cell assays were carried out in nonsaturated conditions and that the expression of MHC-I molecules was taking into account in the results. Each graph is one representative of at least three independent experiments. Data are given as mean±SEM. *P<0.05, P<0.01, *P<0.001 (unpaired student t test).

FIG. 1C-1F: Madra.HCl slows down the growth of tumor bearing intron-derived SL8 epitope Wild type MCA205 sarcoma cells or MCA205 sarcoma cells expressing the globin-SL8-intron construct (MCA205 globin-SL8-intron) were subcutaneously inoculated into the flank of immunocompetent C57BL/6 mice subsequently injected intraperitoneally with 20 mg/kg or 40 mg/kg of Madra.HCl at day 4, 7, 10 and 14 post tumor inoculation. Tumor size was assessed every 3 to 4 days until the established ethical endpoints were reached. The panel C represents the growth curve of MCA205 sarcoma cells expressing the globin-SL8-intron construct (MCA205 globin-SL8-intron), the panel D represents the tumor size at day 25. The panel E represents the growth curve of Wild type MCA205 sarcoma cells (MCA205 WT), the panel F represents the tumor size at day 21. Data are given as mean±SEM. *p<0.05, **p<0.01 (ANOVA with Tukey's multiple comparison test comparing all groups).

FIG. 1G: Madra.HCl extends overall survival of mice bearing intron-derived SL8-expressing tumors Kaplan-Meier survival curve of mice injected subcutaneously with MCA205 globin-SL8-intron and subsequently treated intraperitoneally with Madra.HCl at 20 mg/kg or 40 mg/kg, 4, 7, 10 and 14 days post tumor inoculation.

FIG. 1H: Madra.HCl induces a long-lasting specific anti-tumor response

Growth curve of MCA205 globin-SL8-intron cells and B16F10 WT cells inoculated at day 100 into the right and the left flank, respectively, of C57BL/6 mice which experienced complete tumor regression after treatment with Madra.HCl.

Figure 2:
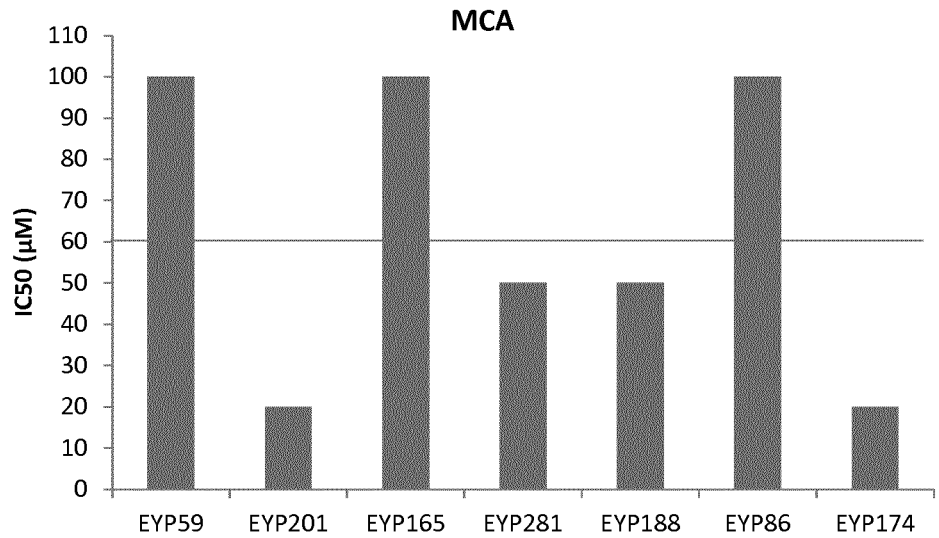
Figure 2:
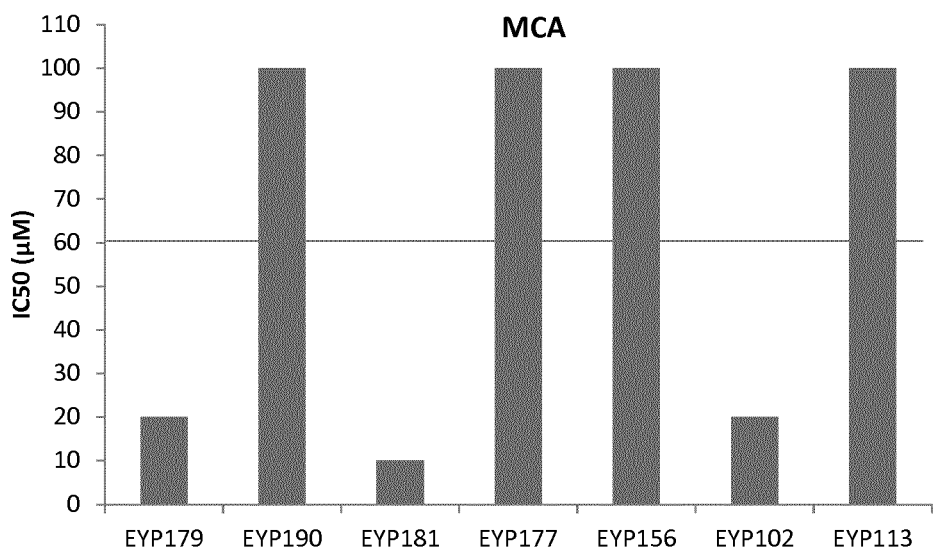
Figure 2:
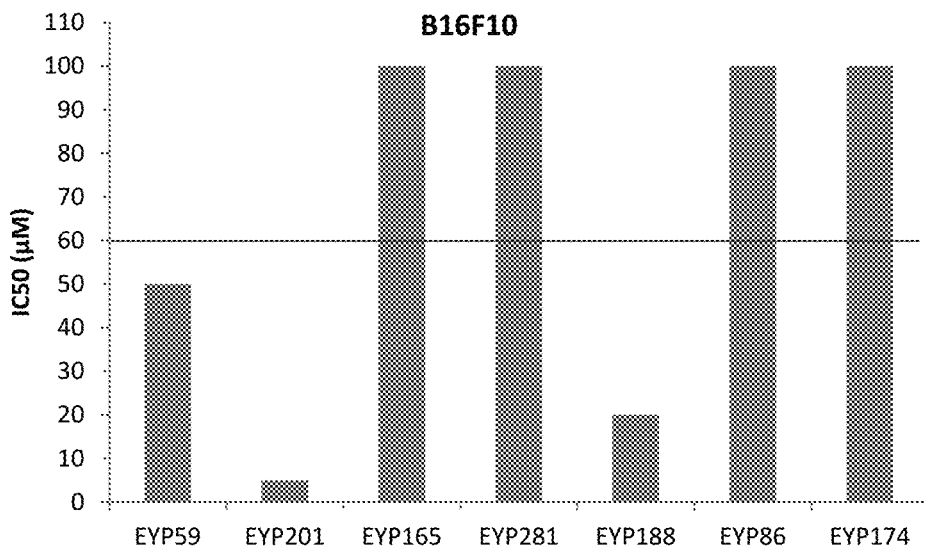
Figure 2:
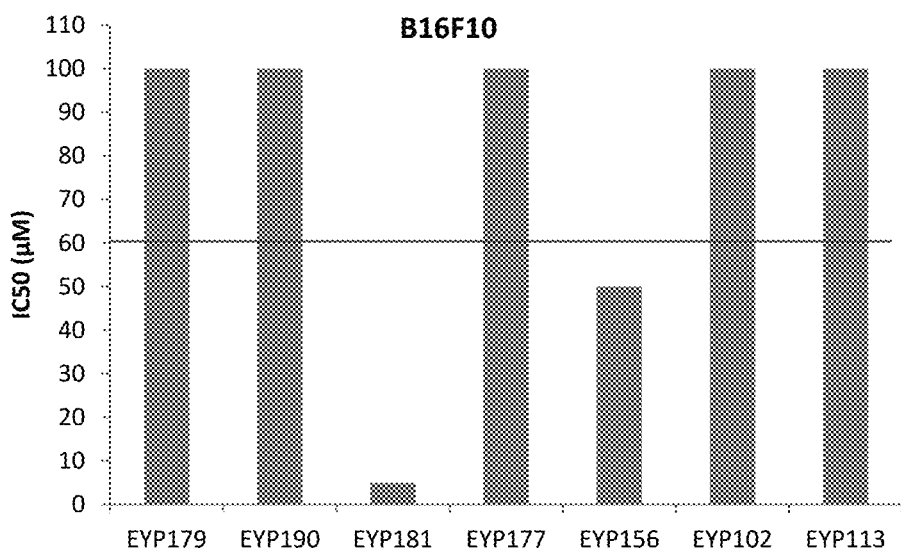

FIG. 2: Test MTT for each derivative of Madrasin

MTT assay performed on MCA205 (A) or B16F10 (B) cells treated with increase doses of the different derivatives of Madrasin. Data are expressed as half maximal inhibitory concentration (IC50) of the different derivatives. The IC50 represents the concentration of the tested compounds that is required for 50% inhibition of the cell viability compared to the control condition. A threshold of 60 µM is notified. It will be the maximum dose used for all the compounds that do not show any cell death.

Figure 3:
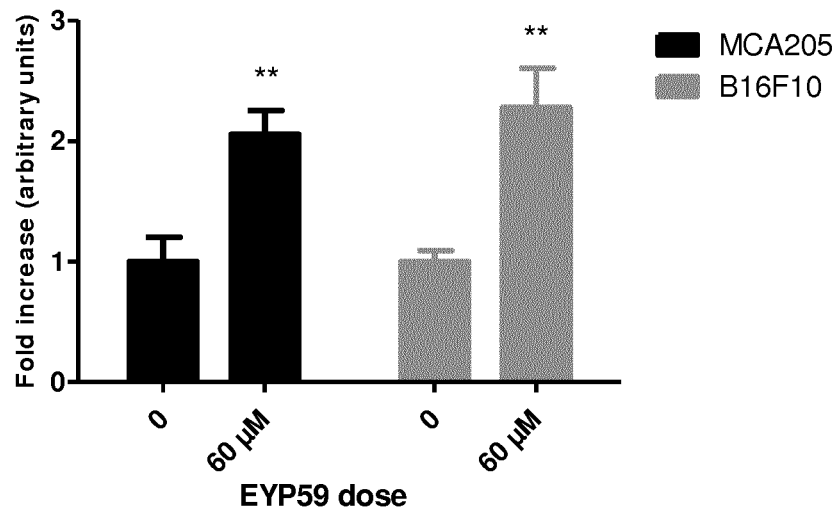
Figure 3:
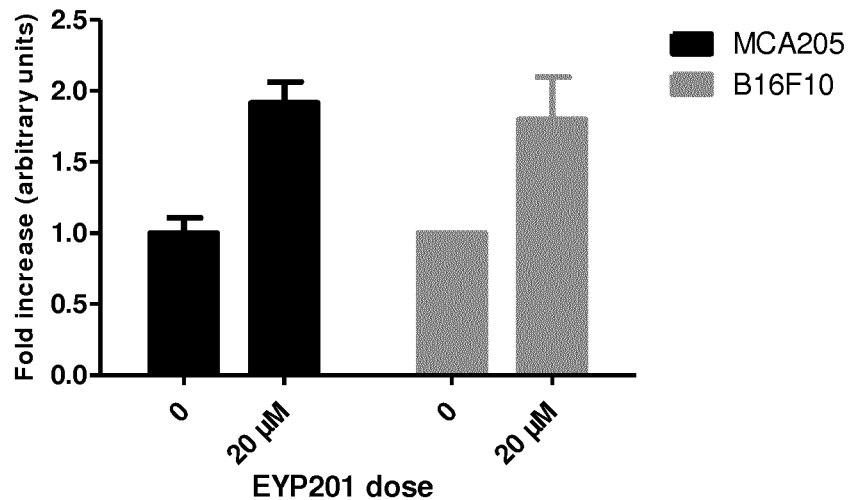
Figure 3:
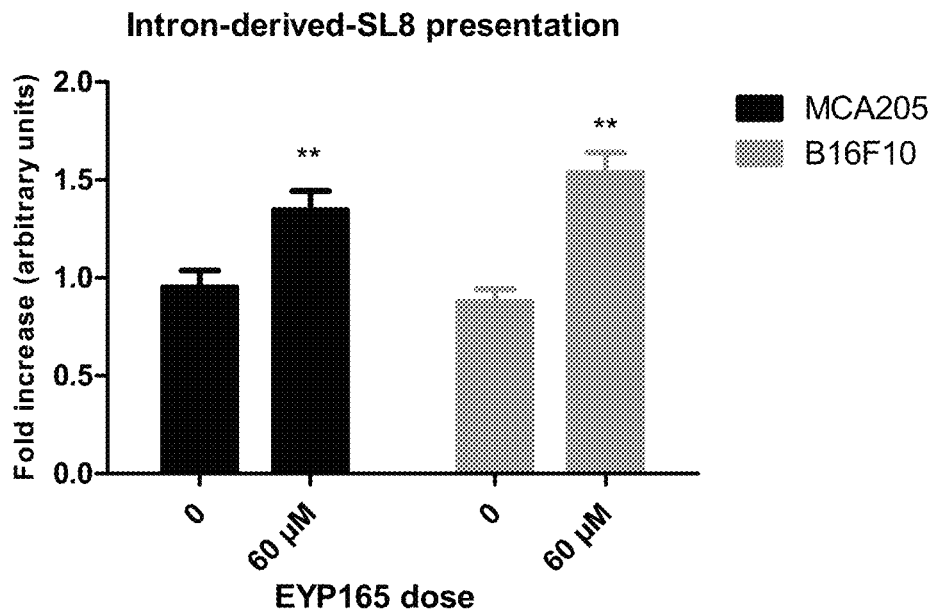
Figure 3:
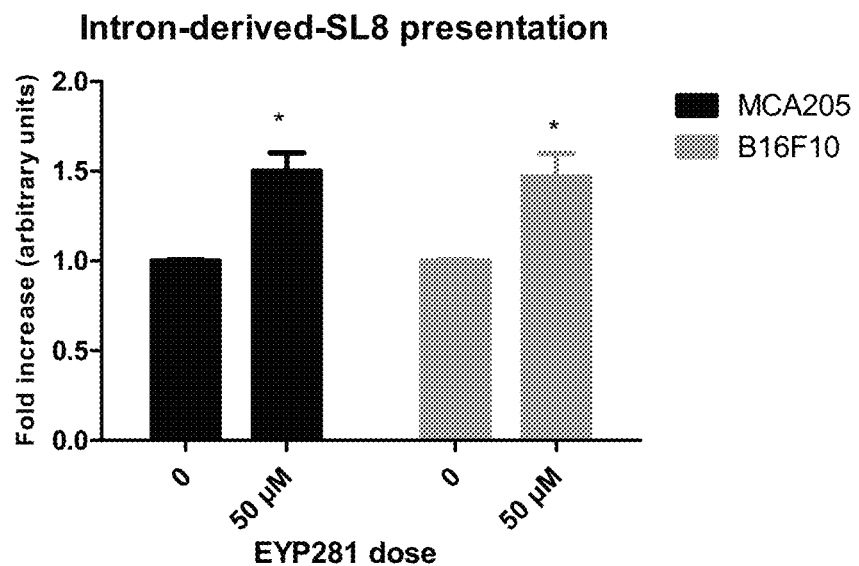

FIG. 3: Derivatives of Madrasin that increase antigen presentation in both murine cell lines.

B3Z specific T-cell activation in MCA205 and B16F10 expressing the intron-derived SL8 antigen after treatment with 60 µM (A) of EYP59 (compound 7), 20 µM (B) of EYP201 (compound 6), 60 µM (C) of EYP165 (compound 57) or 50 µM (D) of EYP281 (compound 32). Free SL8 peptide was added in each condition to ensure that T-cell assays were carried out in nonsaturated conditions and that the expression of MHC-I molecules was taken into account in the results. Each graph is one representative of at least three independent experiments. Data are given as mean±SEM. *P<0.05, P<0.01, *P<0.001 (unpaired student t test).

Figure 4:
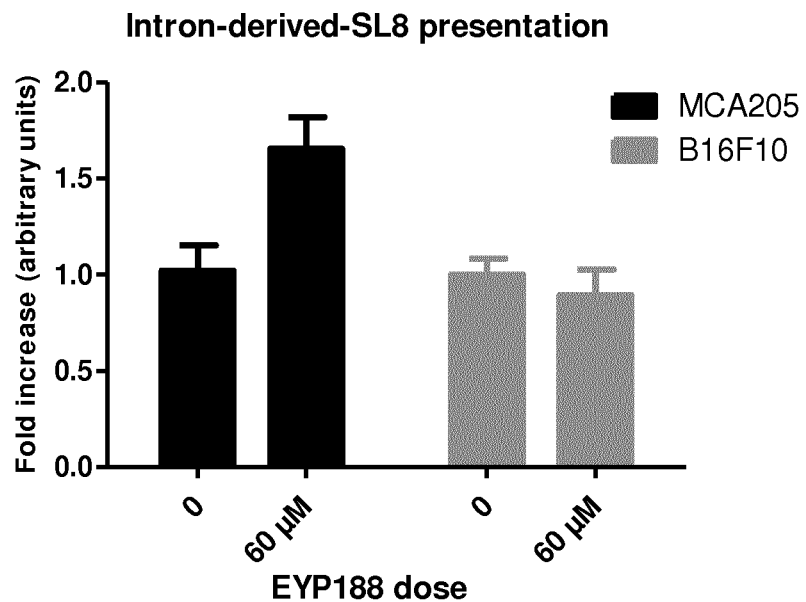
Figure 4:
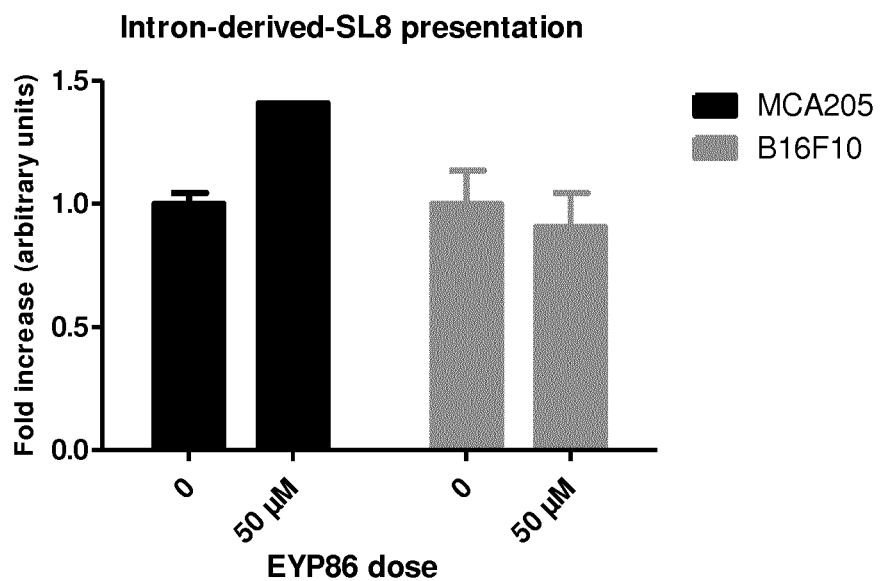

FIG. 4: Derivatives of Madrasin that increase antigen presentation only in MCA205 sarcoma cell line.

B3Z specific T-cell activation in MCA205 expressing the intron-derived SL8 antigen after treatment with 60 µM (A) of EYP188 (compound 42), 50 µM (B) of EYP86 (compound 10). Free SL8 peptide was added in each condition to ensure that T-cell assays were carried out in nonsaturated conditions and that the expression of MHC-I molecules was taken into account in the results. Each graph is one representative of at least three independent experiments. Data are given as mean±SEM. *P<0.05, P<0.01, *P<0.001 (unpaired student t test).

Figure 5:
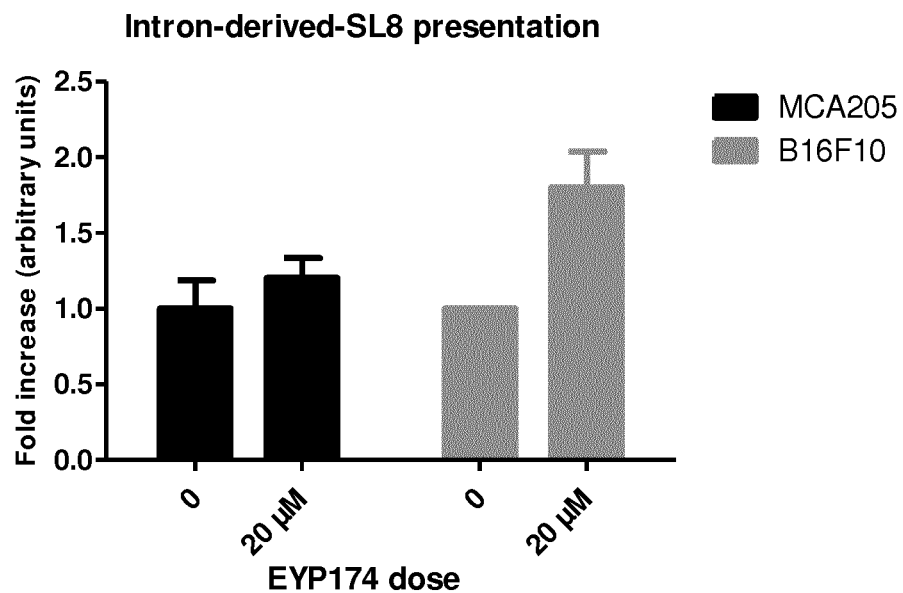
Figure 5:
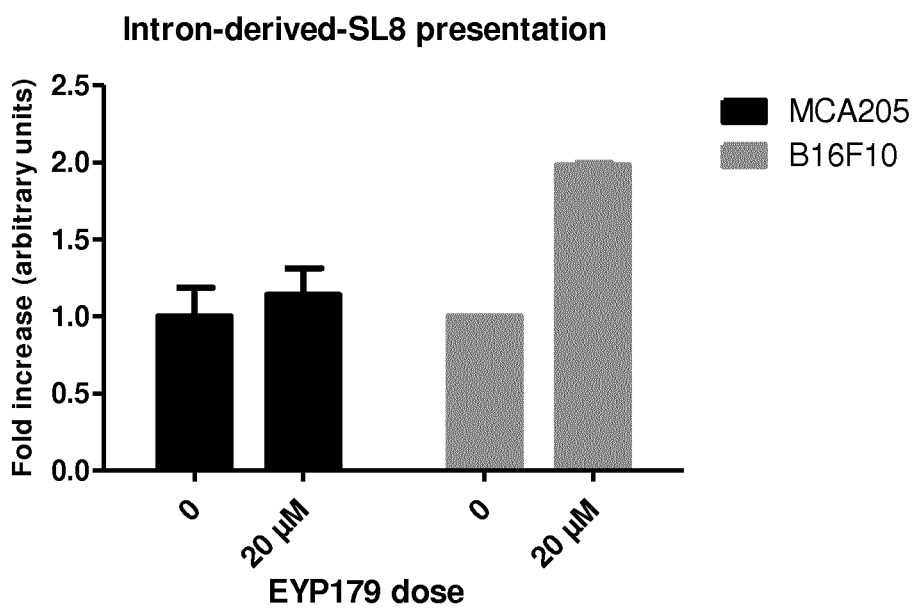
Figure 5:
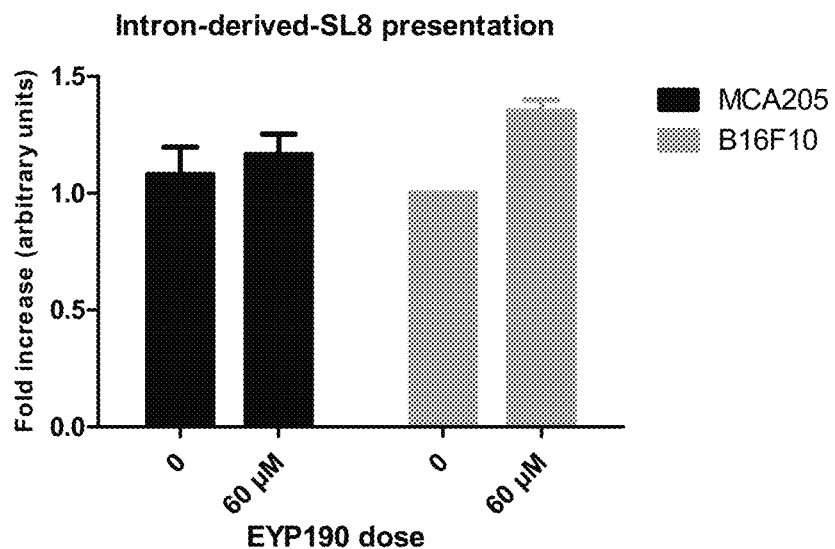
Figure 5:
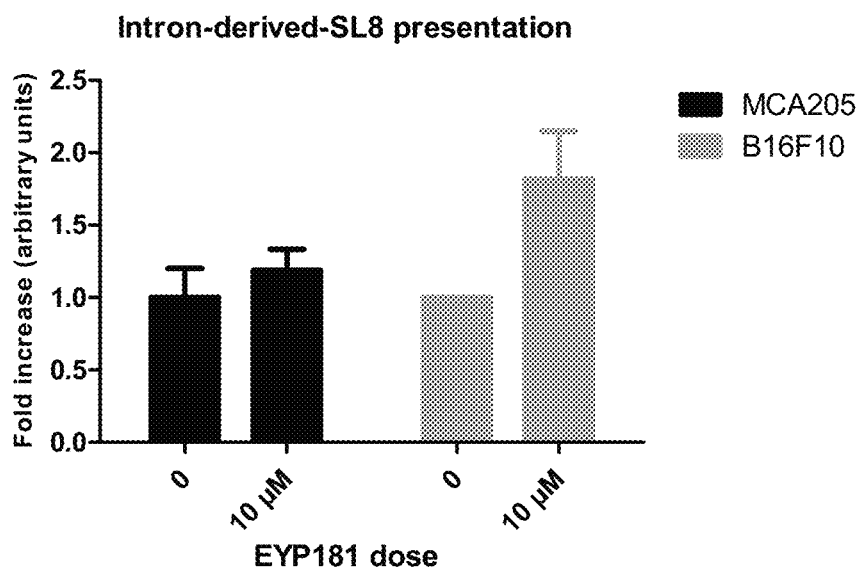

FIG. 5: Derivatives of Madrasin that increase antigen presentation only in B16F10 melanoma cell line.

B3Z specific T-cell activation in MCA205 expressing the intron-derived SL8 antigen after treatment with 20 µM (A) of EYP174 (compound 41), 20 µM (B) of EYP179 (compound 50), 60 µM (C) of EYP190 (compound 54) and 10 µM (D) of EYP181 (compound 49). Free SL8 peptide was added in each condition to ensure that T-cell assays were carried out in nonsaturated conditions and that the expression of MHC-I molecules was taking into account in the results. Each graph is one representative of at least three independent experiments. Data are given as mean±SEM. *P<0.05, P<0.01, *P<0.001 (unpaired student t test).

Figure 6:
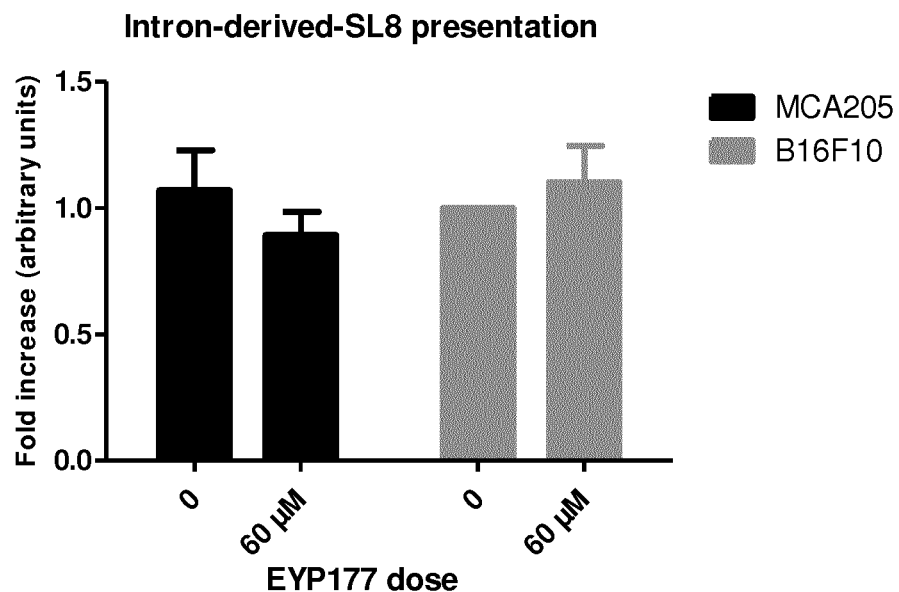
Figure 6:
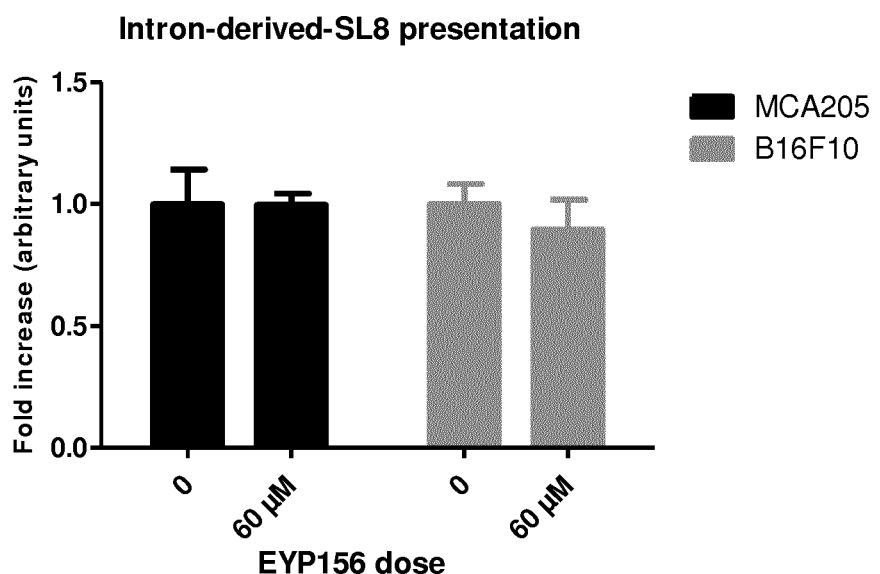
Figure 6:
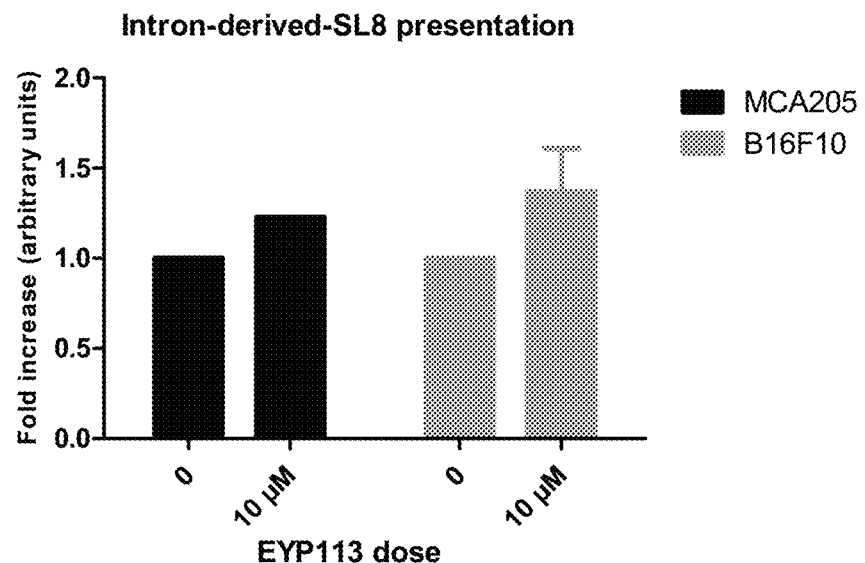
Figure 6:
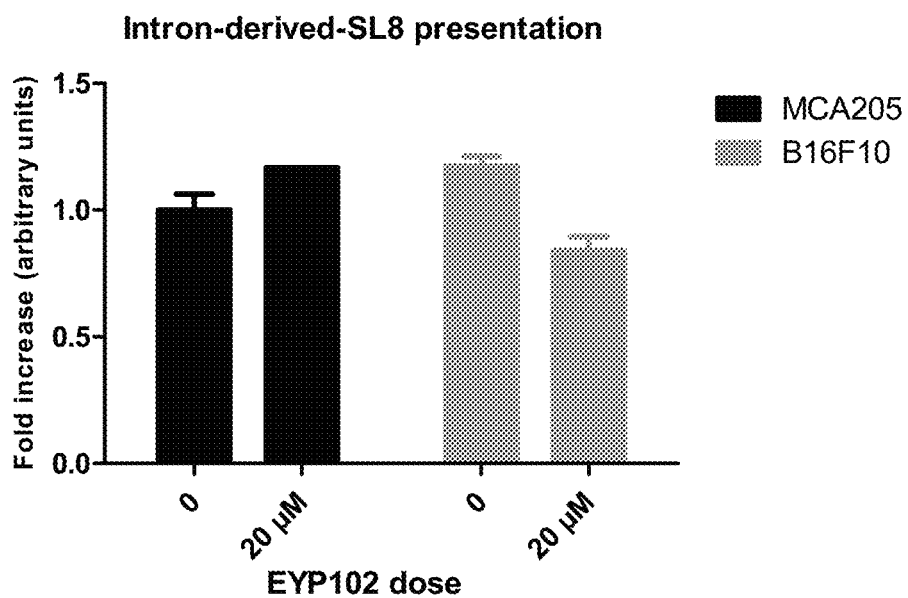

FIG. 6: Derivatives of Madrasin that do not increase antigen presentation in both tumor cell lines.

B3Z specific T-cell activation in MCA205 expressing the intron-derived SL8 antigen after treatment with 60 µM (A) of EYP177 (compound 46), 60 µM (B) of EYP156 (compound 43), 10 µM (C) of EYP113 (compound 11) and 20 µM (D) of EYP102 (compound 9). Free SL8 peptide was added in each condition to ensure that T-cell assays were carried out in nonsaturated conditions and that the expression of MHC-I molecules was taking into account in the results. Each graph is one representative of at least three independent experiments. Data are given as mean±SEM. *P<0.05, P<0.01, *P<0.001 (unpaired student t test).

Figure 7:
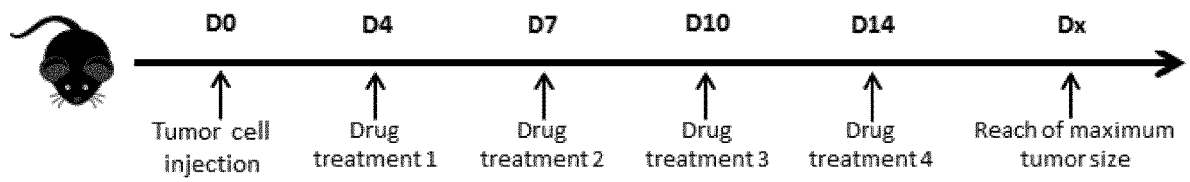
Figure 7:
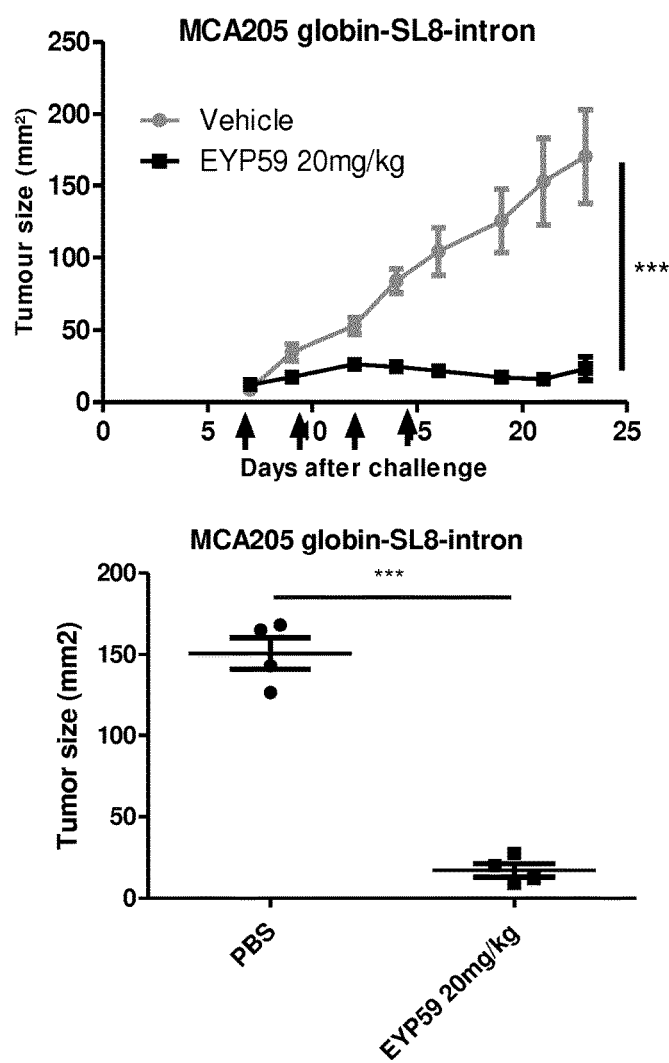
Figure 7:
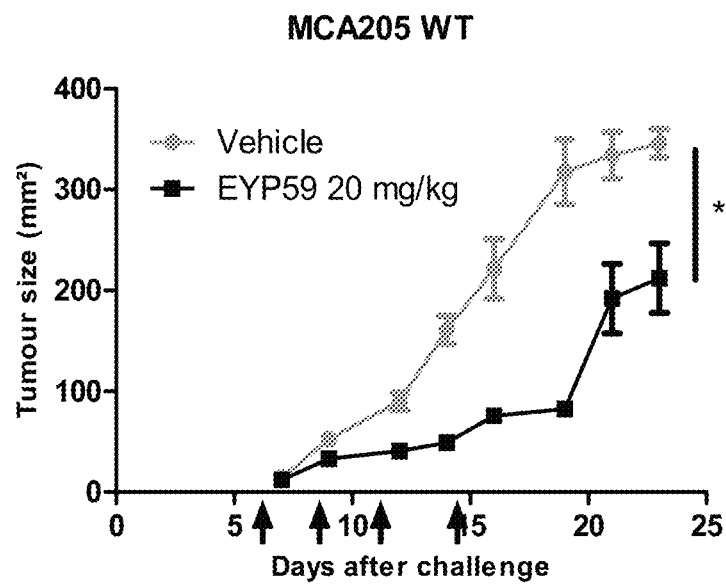
Figure 7:
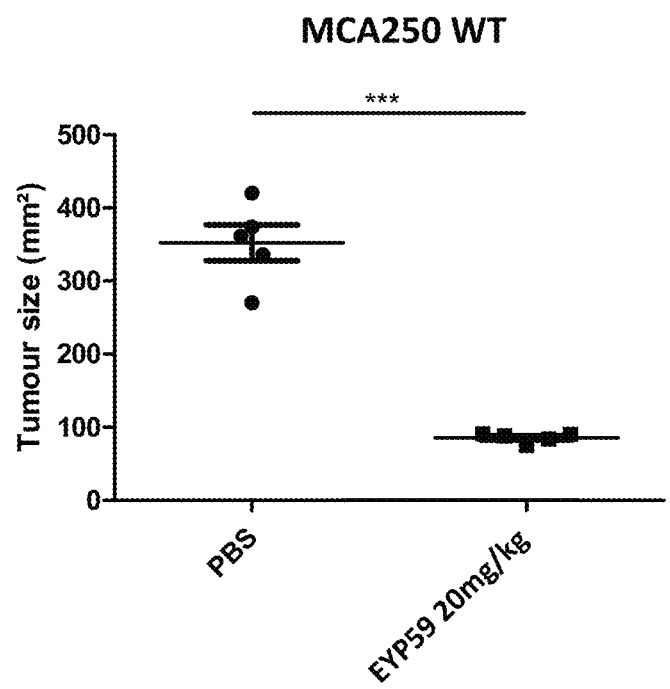
Figure 7:
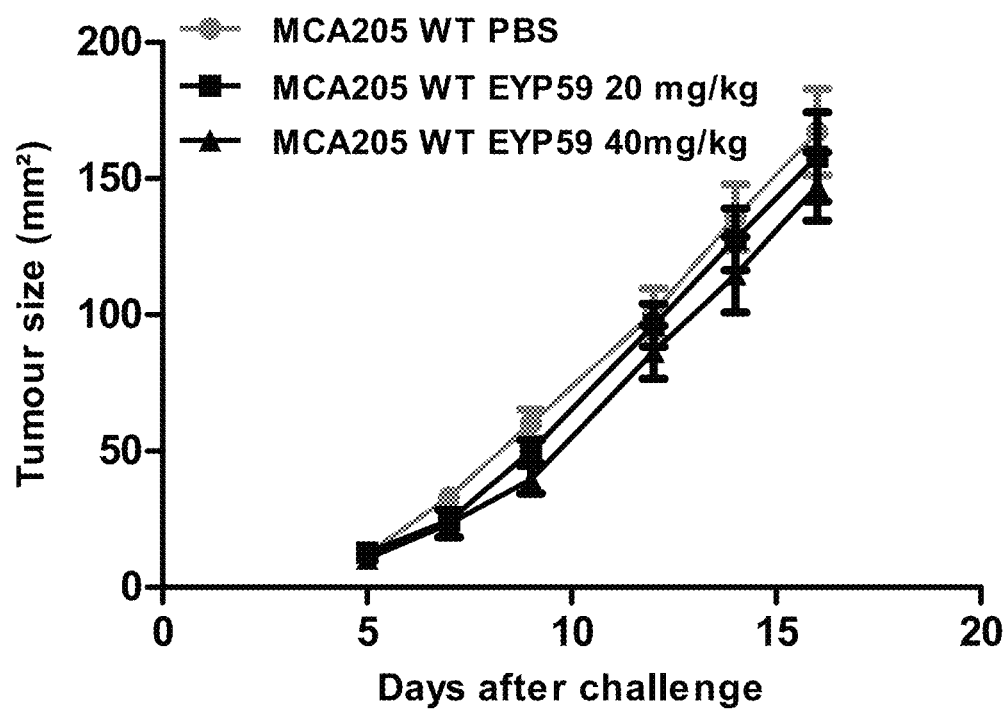

FIG. 7: EYP59 (compound 7) slows down the growth of MCA-WT sarcoma and MCA-intron-SL8.

Wild type MCA205 sarcoma cells or MCA205 sarcoma cells expressing the globin-SL8-intron construct (MCA205 globin-SL8-intron) were subcutaneously inoculated into the flank of immunocompetent C57BL/6 mice subsequently injected intraperitoneally with 20 mg/kg of EYP59 at day 4, 7, 10 and 14 post tumor inoculation. Tumor size was assessed every 3 to 4 days until the established ethical endpoints were reached (A). The upper panel B represents the growth curve of MCA205 sarcoma cells expressing the globin-SL8-intron construct (MCA205 globin-SL8-intron), the lower panel B represents the tumor size at day 23. The upper panel C represents the growth curve of Wild type MCA205 sarcoma cells (MCA205 WT), the lower panel C represents the tumor size at day 19. The panel D represents the growth curve of Wild type MCA205 sarcoma cells (MCA205 WT) in immunodeficient nu/nu mice with the same settings as previously described for the immunocompetent mice. Data are given as mean±SEM. *p<0.05, **p<0.01 (ANOVA with Tukey's multiple comparison test comparing all groups).

Figure 8:
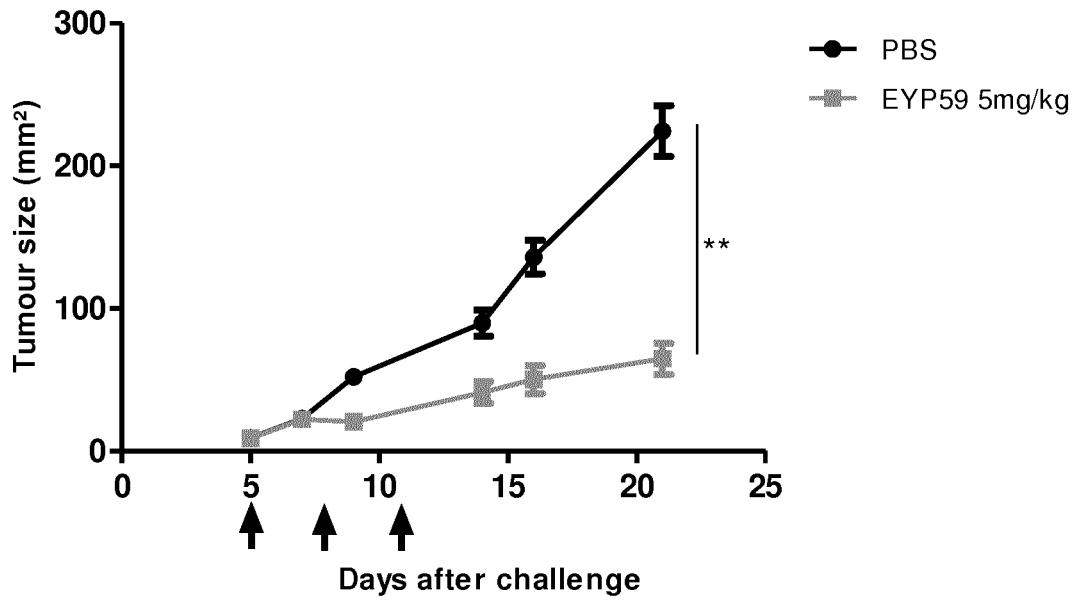
Figure 8:
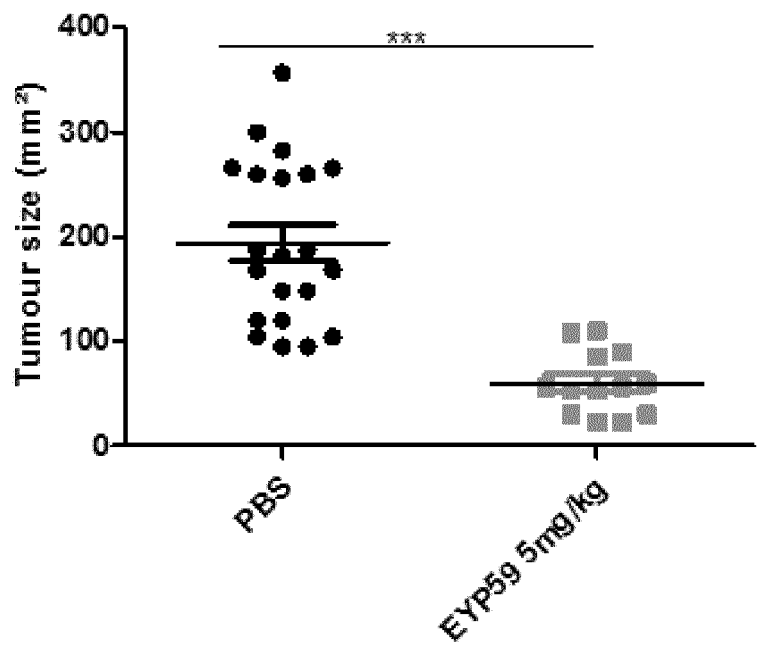
Figure 8:
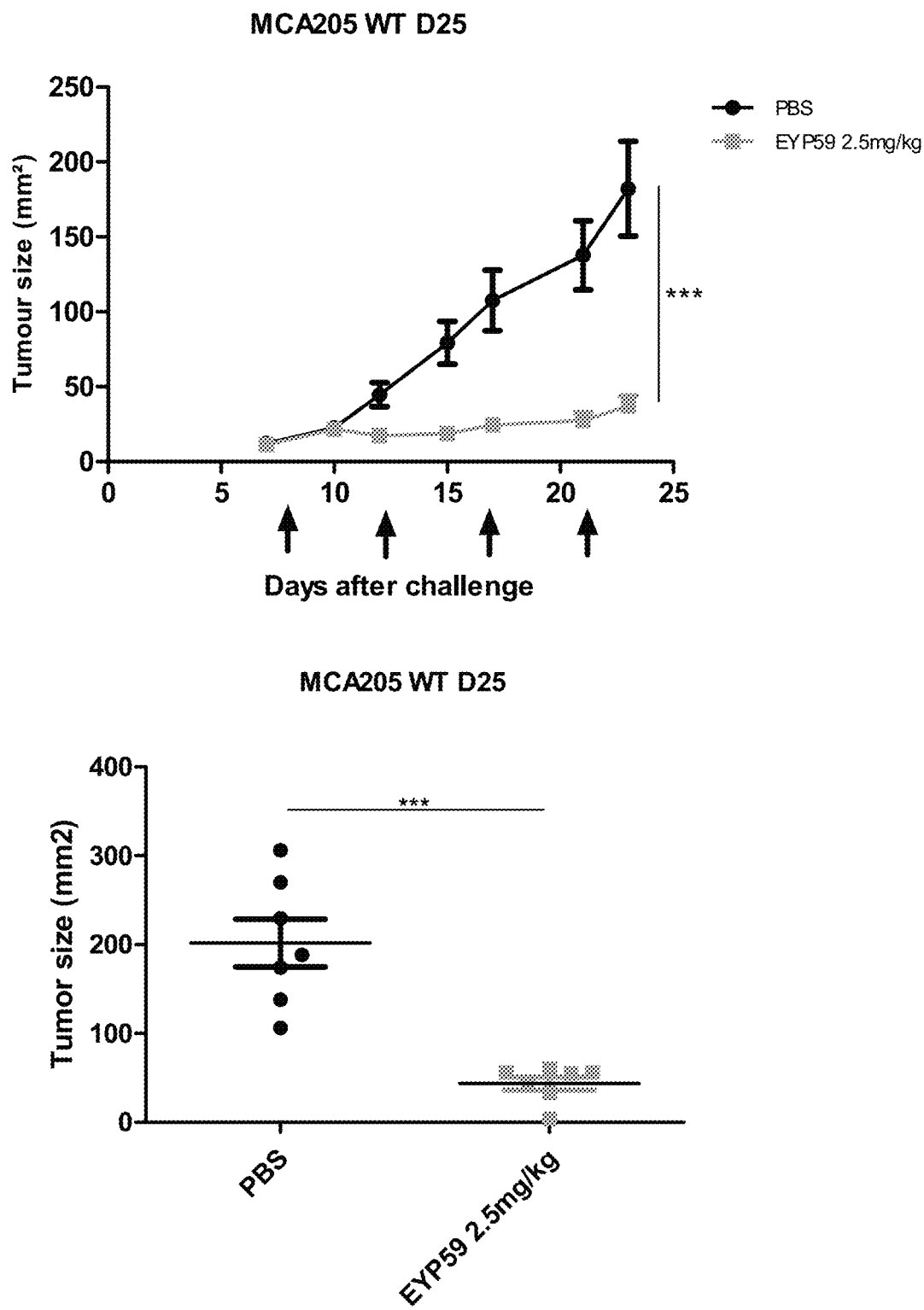

FIG. 8: Madrasin derivative EYP59 (compound 7) efficiently reduces tumor growth in vivo when injected in intratumoral or intravenous ways.

Wild type MCA205 sarcoma cells were subcutaneously inoculated into the flank of immunocompetent C57BL/6 mice subsequently injected intratumorally with 2.5 mg/kg of EYP59 at day 4, 7, 10 and 14 post tumor inoculation or intravenously with 5 mg/kg of EYP59 at day 4, 7, 10 and 14 post tumor inoculation. The upper panel A represents the growth curve of wild type MCA205 sarcoma cells, the lower panel A represents the tumor size at day 21. The upper panel B represents the growth curve of wild type MCA205 sarcoma cell, the lower panel B represents the tumor size at day 25. Data are given as mean±SEM. *p<0.05, **p<0.01 (ANOVA with Tukey's multiple comparison test comparing all groups).

Figure 9:
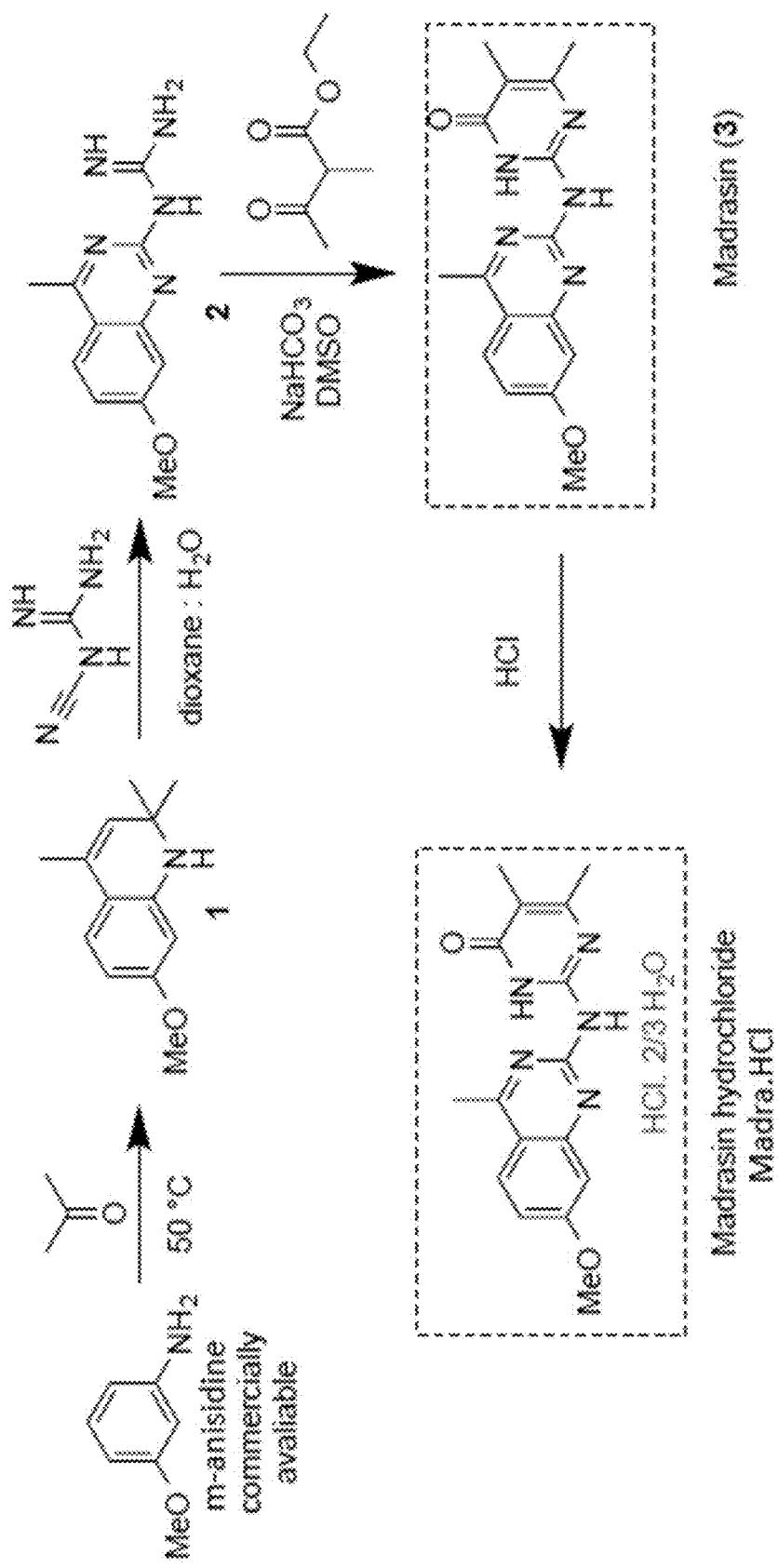

FIG. 9: Synthesis of Madrasin and Madrasin hydrochloride (Madra.HCl).

Figure 10:
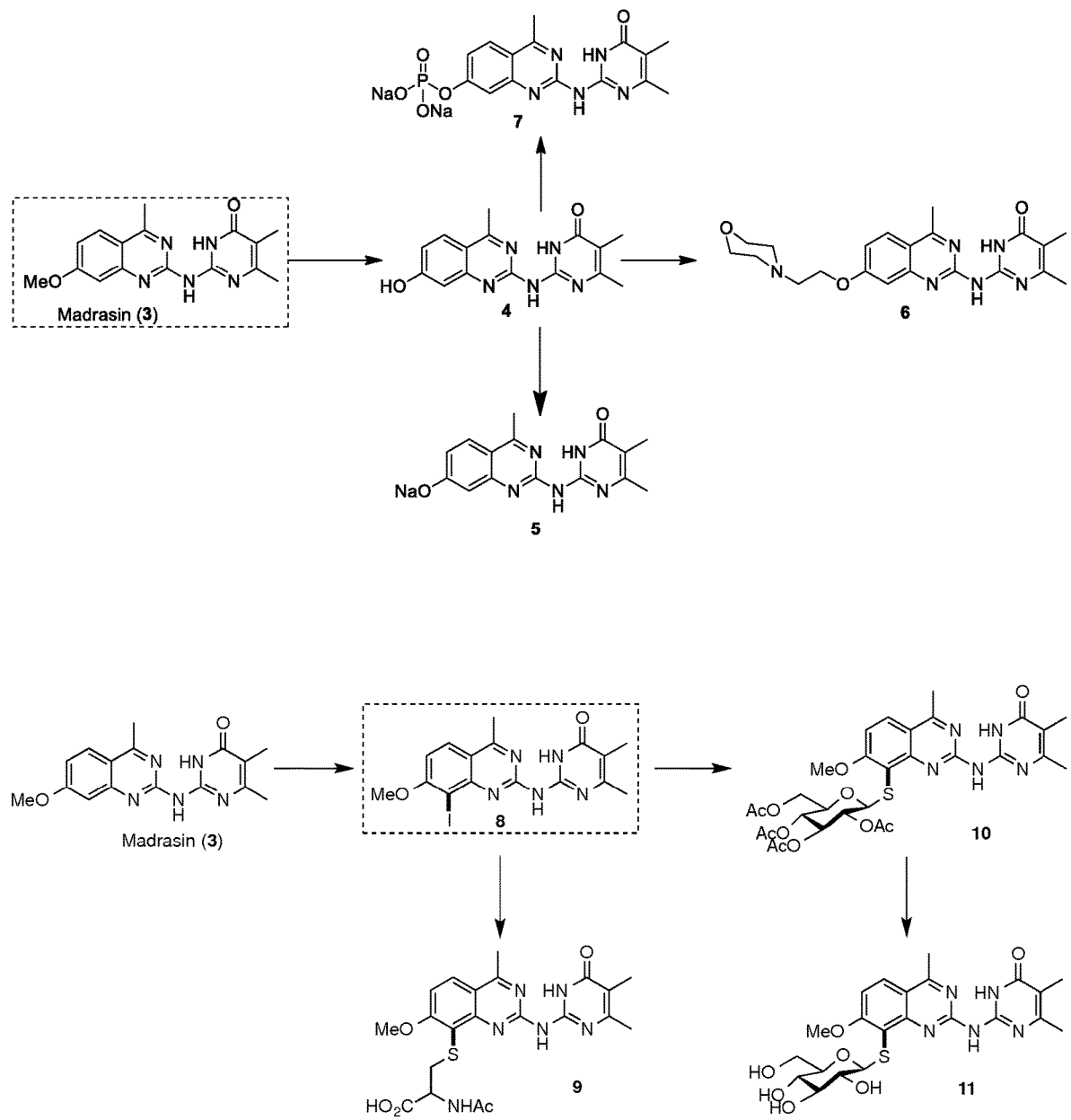
Figure 10:
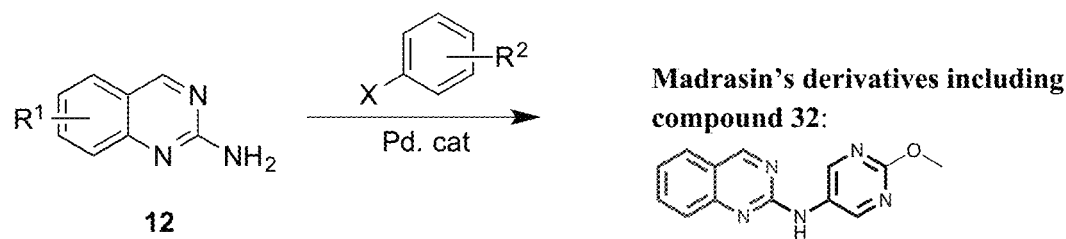
Figure 10:
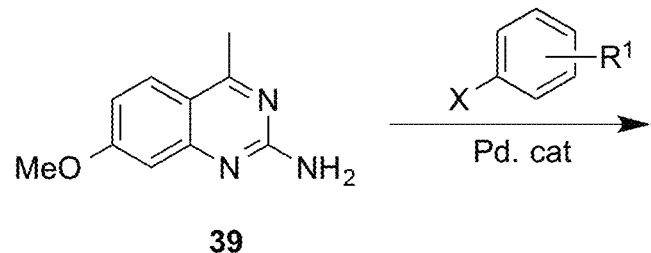

FIG. 10: Pharmacomodulation of Madrasin and synthesis of Madrasin's derivatives.

EXAMPLES

Materials & Methods

Cell Culture

MCA205 mouse sarcoma cell line is cultured at 37° C. under 5% $CO_2$ in RPMI 1640 medium (Life Technologies) in the presence of 1% glutamine, 1% sodium pyruvate, 1% non-essential amino-acids, 1% penicillin/streptomycin and 10% FBS (Life Technologies). B16F10 mouse melanoma cell line is cultured at 37° C. under 5% $CO_2$ in DMEM medium (Life Technologies) containing 1% glutamine, 1% penicillin/streptomycin and 10% FCS under standard conditions. Stable MCA205-Globin-SL8-intron cell line are cultured under the same condition as MCA205 cell line with additional 500 µg/ml G418 (Life Technologies) for selection. Stable B16F10-Globin-SL8-intron cell line are cultured under the same condition as B16F10 cell line with additional 500 µg/ml G418 (Life Technologies) for selection. The SL8/Kb-specific (B3Z) T-cell reporter hybridoma are cultured at 37° C. under 5% $CO_2$ in RPMI 1640 medium (Life Technologies) in the presence of 1% L-glutamine, 1% penicillin/streptomycin, 50 µM β-mercaptoéthanol and 10% FCS.

Schema of Synthesis of Madrasin and all the Derivatives Compounds

1) Synthesis of Madrasin and Madrasin Hydrochloride (Madra.HCL)

Under argon, m-anisidine (2.3 mL, 20.3 mmol) and $InCl_3$ (232 mg, 1.03 mmol) in acetone (30 mL) was heated at 50° C. for 14 h. The solvent was removed and the crude partitioned between DCM and aqueous saturated solution of $Na_2CO_3$. The organic layer was dried over $MgSO_4$, filtered and concentrated. Purification by column chromatography (Cyclohexane/EtOAc 100:0→99:1) afforded the desired compound as a yellowish solid. The spectroscopic data are in accordance with the literature (Tamariz, J. et al. *J. Org. Chem.* 2013, 78, 9614-9626). Yield: 61% (2.51 g, 12.3 mmol). Mp 68.8° C. TLC Rf: 0.5 (Cyclo/EtOAc 9:1). $^1$H NMR (300 MHz, $CDCl_3$) δ 6.97 (d, J=8.4 Hz, 1H), 6.20 (dd, J=8.4, 2.5 Hz, 1H), 6.01 (d, J=2.5 Hz, 1H), 5.19 (s, 1H), 3.75 (s, 3H), 1.96 (d, J=1.5 Hz, 3H), 1.26 (s, 6H). HRMS (ESI) $(M+H)^+$ m/z calculated for $C_{13}H_{18}NO$ 204.1388, found 204.1385.

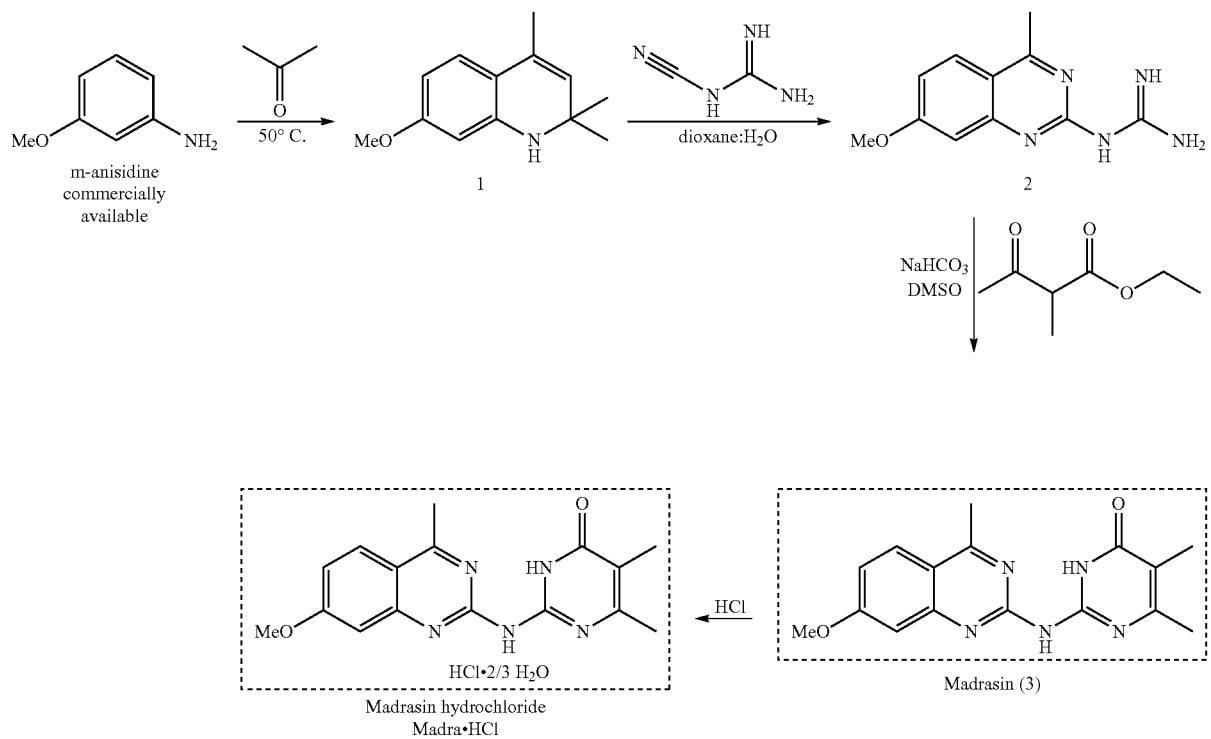

a. 7-Methoxy-2,2,4-trimethyl-1,2-dihydroquinoline (Compound 1) (Ref *Org. Lett.* 2015, 17, 4125)

b. 1-(7-Methoxy-4-methylquinazolin-2-yl)guanidine (Compound 2)

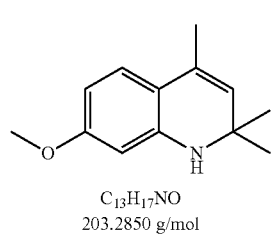

$C_{13}H_{17}NO$
203.2850 g/mol

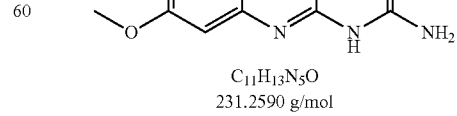

$C_{11}H_{13}N_5O$
231.2590 g/mol 7-methoxy-2,2,4-trimethyl-1,2-dihydroquinoline (compound 1) (2.0 g, 0.98 mmol) and HCl (0.25 mL, 0.98 mmol, 4 M in dioxane) was stirred at room temperature for 30 min. Then H$_2$O (95 mL) and dicyandiamide (831 mg, 0.98 mmol) was added and the mixture was refluxed for 48 h. After cooling at 60° C., the oil was filtered and the pH was adjusted to 11 with an aqueous saturated solution of NaHCO$_3$. The precipitate formed was filtered off and dried in vacuo. The compound 2 was isolated as an off-white powder. Yield: 78% (1.76 g, 0.76 mmol). Mp 235-236° C. $^1$H NMR (300 MHz, DMSO-d$_6$) δ 7.95 (d, J=9.1 Hz, 1H), 7.82 (s, 2H), 7.11 (d, J=2.5 Hz, 1H), 7.00 (dd, J=9.0, 2.5 Hz, 1H), 3.90 (s, 3H), 2.70 (s, 3H). HRMS (ESI) (M+H)$^+$ m/z calculated for C$_{11}$H$_{14}$N$_5$O 232.1198, found 232.1193.

c. 2-((7-Methoxy-4-methylquinazolin-2-yl)amino)-5,6-dimethylpyrimidin-4(3H)-one (Madrasin, Compound 3)

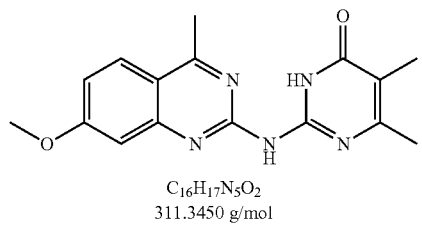

C$_{16}$H$_{17}$N$_5$O$_2$
311.3450 g/mol

A solution of 1-(7-methoxy-4-methylquinazolin-2-yl)guanidine (compound 2) (3.2 g, 13.8 mmol), ethyl 2-methyl-3-oxobutanoate (2.3 mL, 16.2 mmol), NaHCO$_3$ (1.43 g, 17 mmol) in DMSO (22 mL) was heated at 110° C. for 48 h. After cooling at room temperature cold water was added. The precipitate formed was filtered off and purified by column chromatography (DCM/MeOH 100:0→98:2) to afford the madrasin 3 as a beige powder. Yield: 83% (3.58 g, 11.5 mmol). Mp 216.4-217.5° C. TLC Rf: 0.26 (DCM/MeOH 98:2). $^1$H NMR (300 MHz, CDCl$_3$) δ 13.25 (s, 1H), 8.54 (s, 1H), 7.86 (d, J=9.1 Hz, 1H), 7.17 (d, J=2.5 Hz, 1H), 7.07 (dd, J=9.1, 2.5 Hz, 1H), 3.98 (s, 3H), 2.80 (s, 3H), 2.27 (s, 3H), 2.06 (s, 3H). HRMS (ESI) (M+H)$^+$ m/z calculated for C$_{16}$H$_{18}$N$_5$O$_2$ 312.1462, found 312.1458.

d. Madrasin Hydrochloride (Madr.HCl, EYP34)

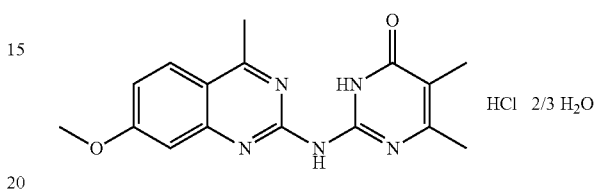

HCl 2/3 H$_2$O

To a solution of madrasin (compound 3) (600 mg, 1.98 mmol) in dry dioxane (10 mL) was added HCl (0.5 mL, 2 mmol, 4 M in dioxane). The mixture was allowed to stir at room temperature for 10 min. The precipitate formed was filtered off and dry in vacuo to afford the Madrasin chlorhydrate salt (565 mg, 1.68 mmol, 85%) as a clear green powder. $^1$H NMR (300 MHz, Deuterium Oxide) δ 7.76 (s, 1H), 6.88 (s, 1H), 6.80 (s, 1H), 3.87 (s, 3H), 2.71 (s, 3H), 2.11 (s, 3H), 1.74 (s, 3H). Mp>330° C. (decomposition). HRMS (ESI) (M+H)$^+$ m/z calculated for C$_{16}$H$_{18}$N$_5$O$_2$ 312.1462, found 312.1460. Anal. Calcd for C$_{16}$H$_{18}$ClN$_5$O$_2$·⅔H$_2$O: C, 53.41; H, 5.42. Found: C, 53.40; H, 5.47.

2) Pharmacomodulation of Madrasin
Part 1:

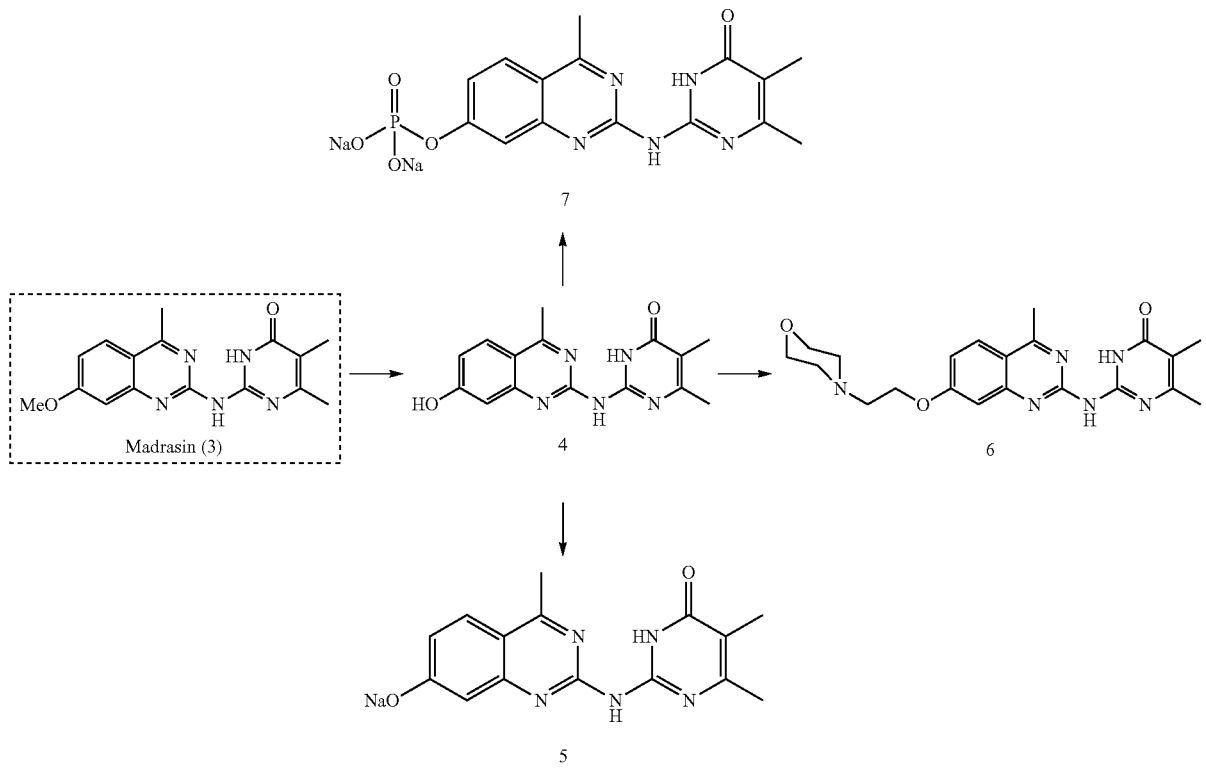

a. 2-((7-Hydroxy-4-methylquinazolin-2-yl)amino)-5,6-dimethylpyrimidin-4(3)-one (Compound 4, EYP107)

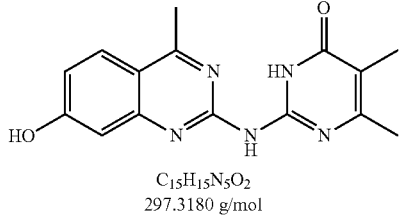 [SMILES: Cc1nc(Nc2nc(C)c3ccc(O)cc3n2)[nH]c(=O)c1C]

$C_{15}H_{15}N_5O_2$
297.3180 g/mol

Under argon, at −78° C., to a solution of Madrasin (compound 3) (250 mg, 0.8 mmol) in DCE (15 mL) was added dropwise BBr$_3$ (12 mL, 12 mmol). The solution was allowed to warm to room temperature and heated at 60° C. for 20 h. After quenching, the solvent was removed under reduced pressure. The crude was taken up with EtOAc and washed with an aqueous saturated solution of NaHCO$_3$. The aqueous layer was extracted 10 times with EtOAc. The combined organic layers were dried over MgSO$_4$, filtered and concentrated. The desired compound 4 was precipitate in DCM, filtered and washed several times with DCM. Yield: 42% (1.0 g, 0.34 mmol). Mp 348.8-349.9° C. TLC Rf: 0.18 (DCM/MeOH 97:3). $^1$H NMR (300 MHz, DMSO) δ 13.52 (s, 1H), 10.93 (s, 2H), 8.05 (d, J=9.0 Hz, 1H), 7.03 (dd, J=9.8, 1.1 Hz, 1H), 6.94 (d, J=2.2 Hz, 1H), 2.77 (s, 3H), 2.18 (s, 3H), 1.90 (s, 3H). HRMS (ESI) (M+H)$^+$ m/z calculated for $C_{15}H_{16}N_5O_2$ 298.1304, found 298.1312.

b. Sodium 2-((4,5-dimethyl-6-oxo-1,6-dihydropyrimidin-2-yl)amino)-4-methyl quinazolin-7-olate (Compound 5, EYP112)

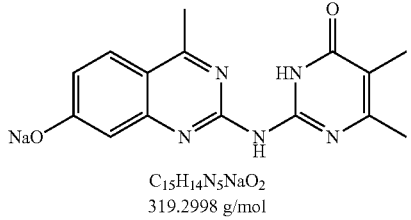

$C_{15}H_{14}N_5NaO_2$
319.2998 g/mol

To a suspension of 2-((7-hydroxy-4-methylquinazolin-2-yl)amino)-5,6-dimethylpyrimidin-4(3H)-one (compound 4) (15 mg, 0.05 mmol) in water (1.5 mL) was added NaOH (50 μL, 0.05 mmol, 1 M in H$_2$O). The stirring was continued for 5 minutes until a clear solution was obtained. After evaporation to dryness, a yellow solid was obtained. Yield: >99% (15 mg, 0.05 mmol). $^1$H NMR (300 MHz, D$_2$O) δ 7.51 (d, J=8.8 Hz, 1H), 6.67 (d, J=8.8 Hz, 1H), 6.40 (s, 1H), 2.49 (s, 3H), 2.03 (s, 3H), 1.71 (s, 3H). HRMS (ESI) (M+H)$^+$ m/z calculated for $C_{15}H_{16}N_5O_2$ 298.1304, found 298.1259.

c. 5,6-Dimethyl-2-((4-methyl-7-(2-morpholinoethoxy)quinazolin-2-yl)amino)pyrimidin-4(3H)-one (Compound 6, EYP201)

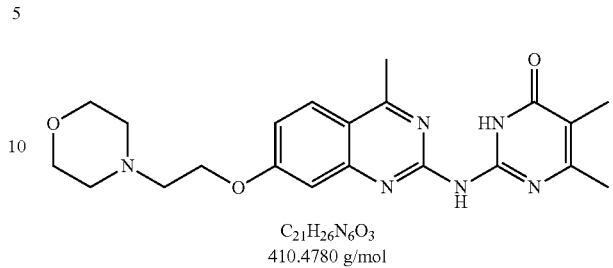

$C_{21}H_{26}N_6O_3$
410.4780 g/mol

Under an inert atmosphere, compound 4 (35 mg, 0.118 mmol) was suspended in DMF (1 mL) and KOH (13 mg, 0.23 mmol) was added. The mixture was stirred at room temperature for 1 h until it became clear. Then 2-chloro-N-ethylmorpholine (22 mg, 0.12 mmol) was added and the mixture was stirred for 14 h at room temperature. The solvent was removed in vacuo. The compound 6 was obtained after column chromatography (DCM/MeOH 100:0→97:3) as a off-white powder. Yield: 19% (9.1 mg, 0.022 mmol). TLC Rf: 0.2 (DCM/MeOH 96:4). $^1$H NMR (300 MHz, CDCl$_3$) δ 13.26 (s, 1H), 7.85 (d, J=9.0 Hz, 1H), 7.19 (s, 1H), 7.08 (d, J=9.0 Hz, 1H), 4.29 (t, J=5.6 Hz, 2H), 3.76 (t, J=4.7 Hz, 4H), 2.89 (t, J=5.7 Hz, 2H), 2.80 (s, 3H), 2.62 (t, J=4.6 Hz, 4H), 2.26 (s, 3H), 2.05 (s, 3H). HRMS (ESI) (M+H)$^+$ m/z calculated for $C_{21}H_{27}N_6O_3$ 411.2145, found 411.2152.

d. Sodium 2-((4,5-dimethyl-6-oxo-1,6-dihydropyrimidin-2-yl)amino)-4-methylquinazolin-7-yl Phosphate (Compound 7, EYP59)

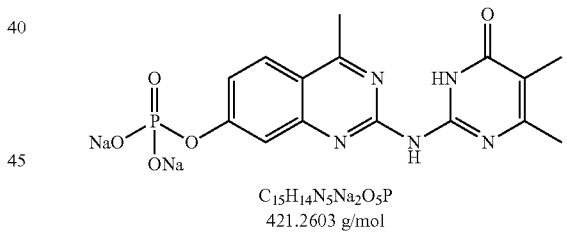

$C_{15}H_{14}N_5Na_2O_5P$
421.2603 g/mol

A suspension of compound 4 (100.4 mg, 0.33 mmol) and KOH (25 mg, 0.44 mmol) in H$_2$O (5 mL) was stirred at room temperature for 30 min. DCM (5 mL) was then added, followed by (EtO)$_2$P(O)Cl (0.064 mL, 0.44 mmol) and TBAB (141 mg, 0.44 mmol). The mixture was stirred at room temperature for 2 h. The organic layer was separated and the aqueous layer was extracted with DCM. The combined organic layers were dried over MgSO$_4$, filtered and concentrated in vacuo. The intermediate diethylphosphate derivative was obtained after column chromatography (DCM/MeOH 100:0→97:3). Yield: 38% (55 mg, 0.12 mmol). $^1$H NMR (300 MHz, CDCl$_3$) δ 13.16 (s, 1H), 7.98 (d, J=9.0 Hz, 1H), 7.66 (d, J=2.3 Hz, 1H), 7.42 (dd, J=9.0, 2.4 Hz, 1H), 4.28 (p, J=7.4 Hz, 4H), 2.84 (s, 3H), 2.27 (s, 3H), 2.05 (s, 3H), 1.39 (t, J=7.0 Hz, 6H).

The purified diethylphosphate (55 mg, 0.12 mmol) compound was then solubilized in DCM (2.5 mL); TMSI was added and the reaction was stirred for 3 h at room temperature. The solvent was evaporated and the crude was triturated with DCM, filtered and then was suspended in $H_2O$. An aqueous solution of NaOH (0.250 mL, 0.254 mmol) was slowly added and the mixture became limpid after 30 min of stirring. The solvent was removed under vacuum to afford Madrasin-phosphate (compound 7). Yield: 93% (50 mg, 0.11 mmol). $^1$H NMR (300 MHz, $D_2O$) δ 7.97 (d, J=9.1 Hz, 1H), 7.47-7.38 (m, 2H), 2.73 (s, 3H), 2.26 (s, 3H), 1.87 (s, 3H). $^{31}$P NMR (81 MHz, $D_2O$) δ −174.17. HRMS (ESI) $(M+H)^+$ m/z calculated for $C_{15}H_{16}N_5NaO_5P$ 400.0787, found 400.0792.

Part 2:

and the pH was adjusted to 5. After extraction with DCM, the organic layers combined were dried over $MgSO_4$, filtered and concentrated. Purification by column chromatography (DCM/MeOH 100:0→98:2) afforded the desired compound 8. Yield: 25% (127 mg, 0.29 mmol). TLC Rf: 0.22 (DCM/MeOH 98:2). $^1$H NMR (300 MHz, $CDCl_3$) δ 13.50 (s, 1H), 8.88 (s, 1H), 7.96 (d, J=9.1 Hz, 1H), 7.09 (d, J=9.1 Hz, 1H), 4.08 (s, 3H), 2.83 (s, 3H), 2.28 (s, 3H), 2.07 (s, 3H). HRMS (ESI) $(M+H)^+$ m/z calculated for $C_{16}H_{17}N_5O_2$ 438.0427, found 438.0427.

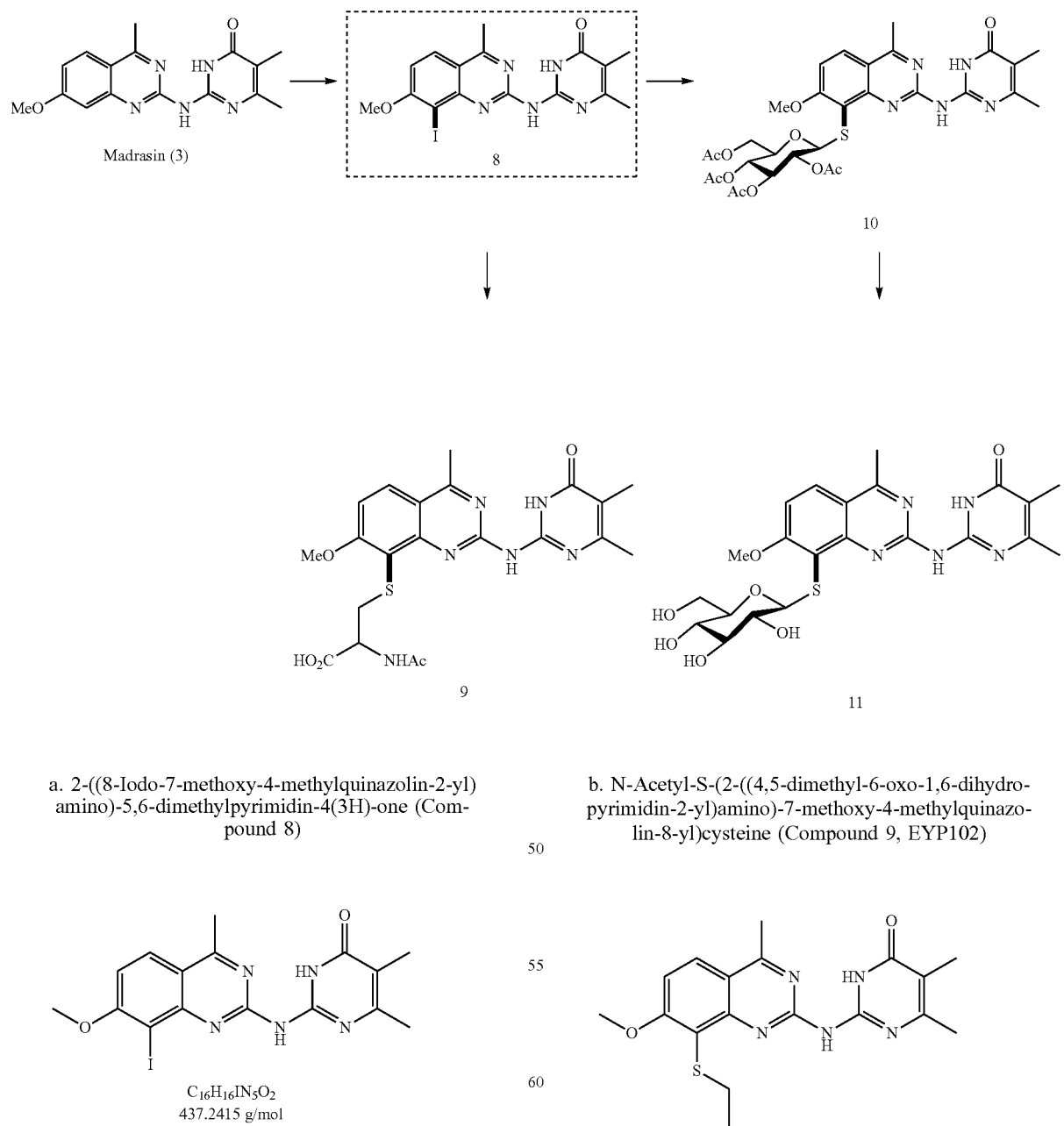

a. 2-((8-Iodo-7-methoxy-4-methylquinazolin-2-yl)amino)-5,6-dimethylpyrimidin-4(3H)-one (Compound 8)

$C_{16}H_{16}IN_5O_2$
437.2415 g/mol

To a cooled solution of Madrasin (compound 3) (360 mg, 1.16 mmol) in $H_2SO_4$ conc. (1.2 mL) was added (in the dark) NIS (248 mg, 1.10 mmol). The solution was stirred at room temperature for 5 h. The mixture was poured in cold water b. N-Acetyl-S-(2-((4,5-dimethyl-6-oxo-1,6-dihydropyrimidin-2-yl)amino)-7-methoxy-4-methylquinazolin-8-yl)cysteine (Compound 9, EYP102)

$C_{21}H_{24}N_6O_5S$
472.5200 g/mol

In a sealable vial, under an inert atmosphere, were added 2-((8-iodo-7-methoxy-4-methylquinazolin-2-yl)amino)-5,6-dimethylpyrimidin-4(3H)-one compound 8 (10.6 mg, 0.025 mmol), cysteine NHAc (7 mg, 0.04 mmol), PdG$_3$Xantphos (5 mg, 0.005 mmol) and THF (0.1 mL). The mixture was purged with argon and NEt$_3$ (10 µL, 0.07 mmol) was added. The mixture was stirred at 50° C. for 18 h and at 70° C. for 6 h. The solvent was removed and purification by column chromatography (DCM/MeOH 100:0→70:30) afforded the desired compound 9. A second purification by preparative TLC was necessary (DCM/MeOH 75:25) to furnish pure compound 9 as a white powder. Yield: 48% (5.7 mg, 0.012 mmol). TLC Rf: 0.1 (DCM/MeOH 8:2). $^1$H NMR (300 MHz, MeOD) δ 8.11 (d, J=9.1 Hz, 1H), 7.32 (d, J=9.0 Hz, 1H), 4.08 (s, 3H), 3.70-3.55 (m, 2H), 2.80 (s, 3H), 2.70 (sl, 1H), 2.23-1.98 (m, 6H), 1.73 (s, 3H). HRMS (ESI) (M+H)$^+$ m/z calculated for $C_{21}H_{25}N_6O_5S$ 473.1607, found 473.1608.

c. ((1S,2S,4R,5S,6S)-5-Acetoxy-7,8-diacetyl-4-((2-((4,5-dimethyl-6-oxo-1,6-dihydropyrimidin-2-yl)amino)-7-methoxy-4-methylquinazolin-8-yl)thio)-3,7λ$^3$,8λ$^3$-trioxabicyclo[4.2.0]octan-2-yl)methyl Acetate (Compound 10, EYP86)

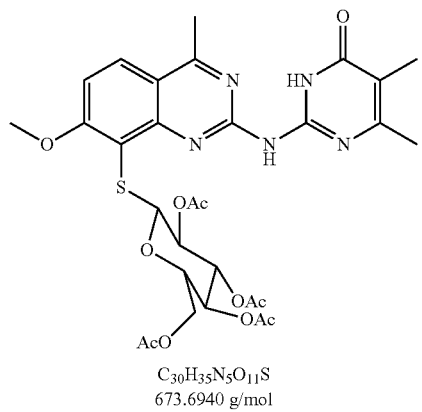

$C_{30}H_{35}N_5O_{11}S$
673.6940 g/mol

Under an inert atmosphere, a solution of 2-((8-iodo-7-methoxy-4-methylquinazolin-2-yl)amino)-5,6-dimethylpyrimidin-4(3H)-one compound 8 (25 mg, 0.055 mmol) and thioglucose (22 mg, 0.06 mmol) in THF (0.5 mL) was purged with argon. The catalyst PdG$_3$Xantphos (10 mg, 0.01 mmol) and Et$_3$N (20 µL, 0.14 mmol) were added and the reaction mixture were heated at 50° C. for 3 h. The solvent was removed in vacuo and purification by column chromatography (DCM/MeOH 100:0→97:3) afforded the desired compound 10 as an orange solid. Yield: 41%. (15.4 mg, 0.022 mmol). TLC Rf: 0.3 (DCM/MeOH 96:4). $^1$H NMR (300 MHz, MeOD) δ 8.18 (d, J=9.1 Hz, 1H), 7.34 (d, J=9.5 Hz, 1H), 5.17 (t, J=9.3 Hz, 1H), 4.75-4.66 (m, 1H), 4.07 (s, 3H), 3.99-3.89 (m, 1H), 3.62-3.52 (m, 2H), 2.83 (s, 3H), 2.62 (s, 2H), 2.10 (s, 6H), 1.94 (d, J=9.4 Hz, 6H), 1.66 (s, 3H). HRMS (ESI) (M+Na)$^+$ m/z calculated for $C_{30}H_{35}N_5O_{11}NaS$ 696.1651, found 696.1657.

d. 2-((7-Methoxy-4-methyl-8-(((2R,3S,4R,5R,6S)-3,4,5-trihydroxy-6-(hydroxymethyl)tetrahydro-2H-pyran-2-yl)thio)quinazolin-2-yl)amino)-5,6-dimethylpyrimidin-4(3H)-one (Compound 11, EYP113)

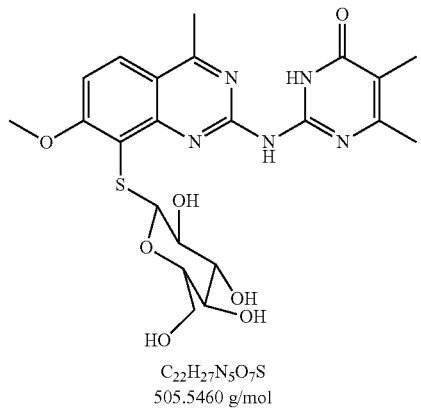

$C_{22}H_{27}N_5O_7S$
505.5460 g/mol

A solution of compound 10 in MeONa (0.19 mL, 0.038 mmol, 0.2 M in MeOH) was stirred at room temperature for 1 h. After evaporation of the solvent in vacuo, compound 11 was obtained as a yellow powder. Yield: >99% (7 mg, 0.014 mmol). $^1$H NMR (300 MHz, MeOD) δ 7.88 (d, J=9.0 Hz, 1H), 7.02 (d, J=9.1 Hz, 1H), 3.87 (s, 3H), 3.53-3.28 (m, 5H), 2.98-2.91 (m, 2H), 2.58 (s, 2H), 2.10 (s, 3H), 1.80 (s, 3H). HRMS (ESI) (M+H)$^+$ m/z calculated for $C_{22}H_{28}N_5O_7S$ 506.1709, found 506.1729.

3) General Procedure A:

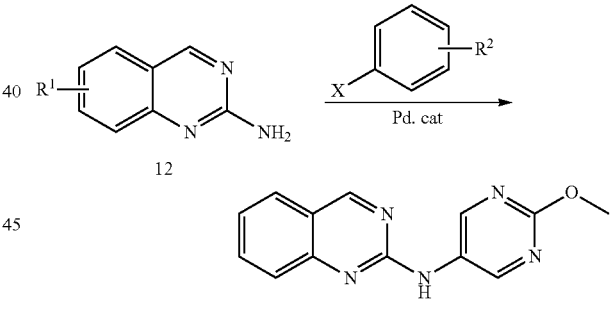

Madrasin's derivatives including compound 32:

Under an inert atmosphere, were added 2-aminoquinazoline derivative (1 equiv) (compound 12), aryl halide (1.5 equiv; unless otherwise stated), Pd$_2$dba$_3$ (7.5 mol % or 10 mol %), Xantphos (15 mol % or 20 mol %) and Cs$_2$CO$_3$ (2 equiv). The mixture was purged with argon. THF was added. The vial was sealed and the reaction mixture was stirred at 80° C. for 14 h. After cooling at room temperature, the solvent was removed under vacuum and the crude was purified by column chromatography to afford the desired compound.

N-(2-Methoxypyrimidin-5-yl)quinazolin-2-amine (Compound 32, EYP281, $C_{13}H_{11}N_5O$, 253,2650 g/mol): Following the general procedure A, starting from 2-aminoquinazoline (21 mg, 0.13 mmol), 5-bromo-2-methoxypyrimidine (26 mg, 0.19 mmol), Pd$_2$dba$_3$ (9 mg, 0.01 mmol), Xantphos (12 mg, 0.02 mmol), Cs$_2$CO$_3$ (84 mg, 0.26 mmol), THF (0.65 mL). Yield: 42% (13 mg, 0.05 mmol). Beige powder. Mp 210.9-211.7° C. TLC Rf: 0.2 (DCM/MeOH 98:2). ¹H NMR (300 MHz, CDCl₃) δ 9.11 (s, 1H), 9.03 (s, 2H), 7.77 (d, J=7.4 Hz, 3H), 7.38 (t, J=7.3 Hz, 1H), 7.21 (s, 1H), 4.04 (s, 3H).

4) Another Series from the Methodology Part

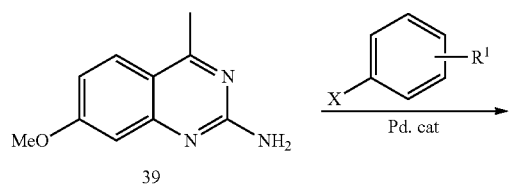

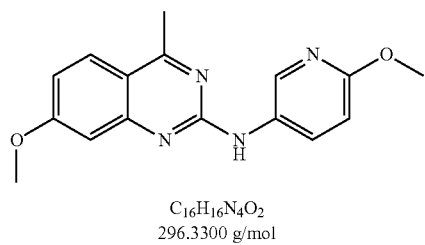 [SMILES: COc1ccc2c(C)nc(Nc3ccc(OC)nc3)nc2c1]

a. 7-Methoxy-N-(6-methoxypyridin-3-yl)-4-methylquinazolin-2-amine (Compound 41, EYP174)

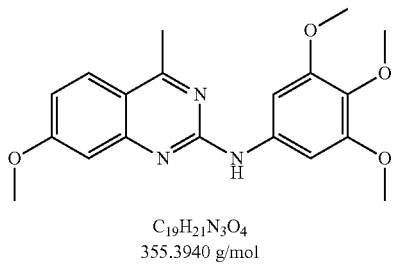 [SMILES: COc1ccc2c(C)nc(Nc3cc(OC)c(OC)c(OC)c3)nc2c1]

$C_{16}H_{16}N_4O_2$
296.3300 g/mol

Following the general procedure A (except that only 1.1 equiv of heteroaryl bromide were used), starting from 2-amino-4-methyl-7-methoxyquinazoline (compound 39) (25 mg, 0.13 mmol), 2-methoxy-5-bromopyridine (0.017 mL, 0.14 mmol), Pd₂dba₃ (12 mg, 0.013 mmol), Xantphos (15 mg, 0.026 mmol), Cs₂CO₃ (84 mg, 0.26 mmol), THF (0.65 mL). Yield: 76% (29 mg, 0.10 mmol). Orange powder. Mp 172.1-173.0° C. TLC Rf: 0.6 (DCM/MeOH 98:2). ¹H NMR (300 MHz, CDCl₃) δ 8.59 (d, J=2.8 Hz, 1H), 8.04 (dd, J=8.8, 2.8 Hz, 1H), 7.75 (d, J=9.1 Hz, 1H), 7.36 (s, 1H), 6.98 (d, J=2.5 Hz, 1H), 6.89 (dd, J=9.0, 2.5 Hz, 1H), 6.76 (d, J=8.8 Hz, 1H), 3.93 (s, 3H), 3.89 (s, 3H), 2.72 (s, 3H). HRMS (ESI) (M+H)⁺ m/z calculated for C₁₆H₁₇N₄O₂ 297.1352, found 297.1328.

b. 7-Methoxy-4-methyl-N-(3,4,5-trimethoxyphenyl) quinazolin-2-amine (Compound 42, EYP188)

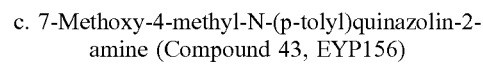

$C_{19}H_{21}N_3O_4$
355.3940 g/mol

Following the general procedure A, starting from 2-amino-4-methyl-7-methoxyquinazoline (compound 39) (25 mg, 0.13 mmol), 1-bromo-3,4,5-trimethoxybenezene (47 mg, 0.19 mmol), Pd₂dba₃ (12 mg, 0.013 mmol), Xantphos (15 mg, 0.026 mmol), Cs₂CO₃ (84 mg, 0.26 mmol), THF (0.65 mL). Yield: 58% (26 mg, 0.07 mmol). Pale yellow powder; Mp 159.5-160.1° C. TLC Rf: 0.8 (DCM/MeOH 98:2). ¹H NMR (300 MHz, CDCl₃) δ 7.78 (d, J=9.0 Hz, 1H), 7.39 (s, 1H), 7.11 (s, 2H), 6.97 (d, J=2.6 Hz, 1H), 6.92 (dt, J=9.0, 2.4 Hz, 1H), 3.91 (s, 3H), 3.89 (s, 6H), 3.83 (s, 3H), 2.75 (s, 3H). HRMS (ESI) (M+H)⁺ m/z calculated for C₁₉H₂₂N₃O₄ 356.1610, found 356.1546.

c. 7-Methoxy-4-methyl-N-(p-tolyl)quinazolin-2-amine (Compound 43, EYP156)

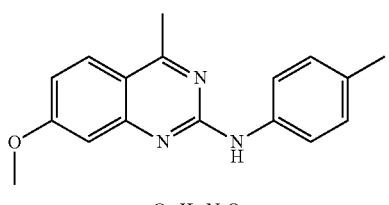

$C_{17}H_{17}N_3O$
279.3430 g/mol

Following the general procedure A, starting from 2-amino-4-methyl-7-methoxyquinazoline (compound 39) (25 mg, 0.13 mmol), 4-bromotoluene (32 mg, 0.19 mmol), Pd₂dba₃ (12 mg, 0.013 mmol), Xantphos (15 mg, 0.026 mmol), Cs₂CO₃ (84 mg, 0.26 mmol), THF (0.65 mL). Yield: 39% (14.0 mg, 0.05 mmol). Off-white solid. Mp 142.8-143.3° C. TLC Rf: 0.7 (DCM 100%). ¹H NMR (300 MHz, CDCl₃) δ 7.77 (d, J=9.0 Hz, 1H), 7.68 (d, J=8.2 Hz, 2H), 7.24-7.12 (m, 3H), 7.05 (d, J=2.5 Hz, 1H), 6.90 (dd, J=9.1, 2.5 Hz, 1H), 3.93 (s, 3H), 2.75 (s, 3H), 2.34 (s, 3H). HRMS (ESI) (M+H)⁺ m/z calculated for C₁₇H₁₈N₃O 280.1450, found 280.1444.

d. t-Butyl 3-((7-methoxy-4-methylquinazolin-2-yl)amino)-1H-indole-1-carboxylate (Compound 46, EYP177)

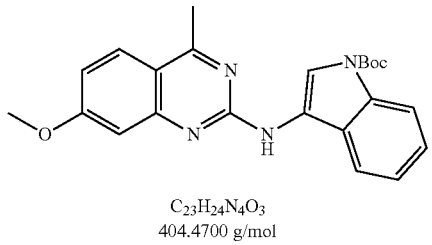 [SMILES: COc1ccc2c(C)nc(Nc3cn(C(=O)OC(C)(C)C)c4ccccc34)nc2c1]

C$_{23}$H$_{24}$N$_4$O$_3$
404.4700 g/mol

Following the general procedure A (except that only 1.1 equiv of heteroaryl bromide were used), starting from 2-amino-4-methyl-7-methoxyquinazoline (compound 39) (25 mg, 0.13 mmol), 3-bromoindole derivative (41 mg, 0.14 mmol), Pd$_2$dba$_3$ (12 mg, 0.013 mmol), Xantphos (15 mg, 0.026 mmol), Cs$_2$CO$_3$ (84 mg, 0.26 mmol), THF (0.65 mL). Yield: 31% (16 mg, 0.04 mmol). Orange powder. Mp 114-116° C. TLC Rf: 0.55 (DCM/MeOH 98:2). $^1$H NMR (300 MHz, CDCl$_3$) δ 8.57 (s, 1H), 8.17 (s, 1H), 7.82 (d, J=9.0 Hz, 1H), 7.58 (d, J=7.7 Hz, 1H), 7.40-7.27 (m, 4H), 7.09 (d, J=2.5 Hz, 1H), 6.94 (dd, J=9.1, 2.5 Hz, 1H), 3.95 (s, 3H), 2.80 (s, 3H), 1.73 (s, 9H). HRMS (ESI) (M+H)$^+$ m/z calculated for C$_{23}$H$_{25}$N$_4$O$_3$ 405.1927, found 405.1932.

e. N$^2$-(7-Methoxy-4-methylquinazolin-2-yl)-N$^4$-methylpyrimidine-2,4-diamine (Compound 49, EYP181)

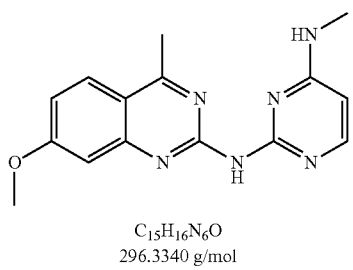 [SMILES: CNc1ccnc(Nc2nc(C)c3ccc(OC)cc3n2)n1]

C$_{15}$H$_{16}$N$_6$O
296.3340 g/mol

Following the general procedure A (except that only 1.1 equiv of heteroaryl chloride were used), starting from 2-amino-4-methyl-7-methoxyquinazoline (compound 39) (25 mg, 0.13 mmol), 2-chloro-N-methylpyrimidin-4-amine (20 mg, 0.14 mmol), Pd$_2$dba$_3$ (12 mg, 0.013 mmol), Xantphos (15 mg, 0.026 mmol), Cs$_2$CO$_3$ (84 mg, 0.26 mmol), THF (0.65 mL). Yield: 31% (11 mg, 0.04 mmol). Grey powder. Mp 247.4-249.1° C. TLC Rf: 0.45 (DCM/MeOH 9:1). $^1$H NMR (300 MHz, MeOD) δ 8.02 (d, J=9.2 Hz, 2H), 7.49 (s, 1H), 7.13 (d, J=9.2 Hz, 1H), 6.39 (d, J=6.5 Hz, 1H), 4.00 (s, 3H), 3.07 (s, 3H), 2.85 (s, 3H). HRMS (ESI) (M+H)$^+$ m/z calculated for C$_{15}$H$_{17}$N$_6$O 297.1464, found 297.1473.

f. 7-Methoxy-N-(4-methoxypyrimidin-2-yl)-4-methylquinazolin-2-amine (Compound 50, EYP179)

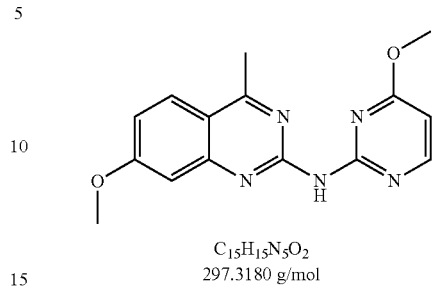

C$_{15}$H$_{15}$N$_5$O$_2$
297.3180 g/mol

Following the general procedure A (except that only 1.1 equiv of heteroaryl chloride were used), starting from 2-amino-4-methyl-7-methoxyquinazoline (compound 39) (25 mg, 0.13 mmol), 2-chloro-4-methoxypyrimidine (20 mg, 0.14 mmol), Pd$_2$dba$_3$ (12 mg, 0.013 mmol), Xantphos (15 mg, 0.026 mmol), Cs$_2$CO$_3$ (84 mg, 0.26 mmol), THF (0.65 mL). Yield: 62% (23 mg, 0.08 mmol). Yellow powder. Mp 160.8-161.5° C. TLC Rf: 0.3 (DCM/MeOH 98:2). $^1$H NMR (300 MHz, CDCl$_3$) δ 8.42-8.33 (m, 1H), 8.28-8.16 (m, 1H), 7.84 (d, J=9.0 Hz, 1H), 7.23 (s, 1H), 7.01 (dd, J=9.0, 2.3 Hz, 1H), 6.35 (d, J=5.6 Hz, 1H), 3.97 (s, 3H), 3.92 (s, 3H), 2.81 (s, 3H). HRMS (ESI) (M+H)$^+$ m/z calculated for C$_{15}$H$_{16}$N$_5$O$_2$ 298.1304, found 298.1302.

g. 7-Methoxy-N-(2-methoxypyrimidin-4-yl)-4-methylquinazolin-2-amine (Compound 54, EYP190)

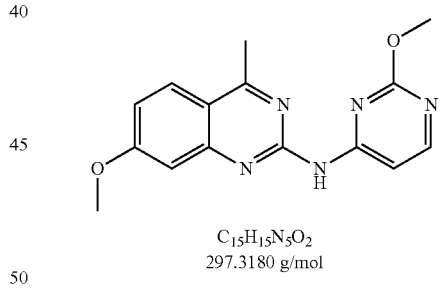

C$_{15}$H$_{15}$N$_5$O$_2$
297.3180 g/mol

To a solution of compound 53 (EYP193) (10 mg, 0.033 mmol) in MeOH (0.5 mL) was added NaOMe (0.15 mL, 0.075 mmol). The mixture was heated at 80° C. for 6 h. The solvent was then removed in vacuo and purification by column chromatography (DCM/MeOH 100:0→99:1) afforded the desired compound 54 as a white solid. Yield: 61% (6 mg, 0.02 mmol). Mp 173.9-174.3° C. TLC Rf: 0.27 (DCM/MeOH 98:2). $^1$H NMR (300 MHz, CDCl$_3$) δ 8.41 (d, J=5.7 Hz, 1H), 8.35 (d, J=5.8 Hz, 1H), 7.96 (s, 1H), 7.86 (d, J=9.0 Hz, 1H), 7.12 (d, J=2.6 Hz, 1H), 7.05 (dd, J=9.1, 2.5 Hz, 1H), 3.98 (s, 3H), 3.97 (s, 3H), 2.81 (s, 3H). HRMS (ESI) (M+H)$^+$ m/z calculated for C$_{15}$H$_{16}$N$_5$O$_2$ 298.1304, found 298.1309.

h. N-(1H-Indol-3-yl)-7-methoxy-4-methylquinazolin-2-amine (Compound 57, EYP165)

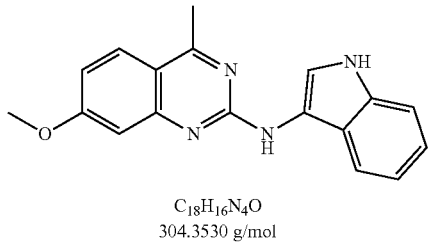 [SMILES: COc1ccc2c(C)nc(Nc3c[nH]c4ccccc34)nc2c1]

$C_{18}H_{16}N_4O$
304.3530 g/mol

To a solution of compound 46 (EYP177) (35 mg, 0.08 mmol) in DCM (2 mL) was added TFA (0.1 mL, 1.3 mmol). The solution was stirred at room temperature for 2 h. After addition of an aqueous saturated solution of $NaHCO_3$ and extraction with DCM, the organic layer was dried over $MgSO_4$, filtered and concentrated to dryness. Purification by column chromatography (DCM/MeOH 100:1→200:1) afforded the desired compound 57 as a white solid. Yield: 48% (11 mg, 0.04 mmol). White powder. TLC Rf: 0.6 (DCM/MeOH 98:2). $^1$H NMR (300 MHz, DMSO-$d_6$) δ 10.69 (s, 1H), 9.51 (s, 1H), 8.17 (s, 1H), 8.01 (d, J=8.0 Hz, 1H), 7.91 (d, J=8.9 Hz, 1H), 7.34 (d, J=8.1 Hz, 1H), 7.09 (t, J=7.5 Hz, 1H), 7.01 (d, J=2.4 Hz, 1H), 6.96 (t, J=7.5 Hz, 1H), 6.88 (dd, J=9.0, 2.5 Hz, 1H), 3.91 (s, 3H), 2.73 (s, 3H). HRMS (ESI) (M+H)$^+$ m/z calculated for $C_{18}H_{17}N_4O$ 305.1402, found 305.1408.

T-Cell Assay

MCA205 and B16F10 mouse cell lines are transfected with the plasmid YFP-Globin-SL8-intron or with the PCDNA3 empty plasmid (negative control) with the transfection reagent jetPRIME (Ozyme) or GeneJuice (Millipore) respectively according to each manufacturer protocol. Twenty-four hours after transfection, cells are treated with different doses of Madrasin (Sigma SML 1409), Madra.HCl (3·HCl) or the different compounds herein cited. Cells are then washed three times with PBS 1× and $5.10^4$ tumor cells are co-cultured with $1.10^5$ B3Z hybridoma in a 96-well plate. In positive control wells, 4 μg/ml of synthetic peptide SL8 is added. Cells are then incubated overnight at 37° C. with 5% $CO_2$. The plate is centrifuged at 1200 rpm for 5 min, cells are washed twice with PBS 1× and lysed for 5 min at 4° C. under shaking in 0.2% TritonX-100, 0.2% DTT, 0.5M $K_2HPO_4$, 0.5M $KH_2PO_4$. The lysate is centrifuged at 3000 rpm for 10 min and the supernatant is transferred to a 96-well optiplate (OptiPlaque-96, PerkinElmer). A revelation buffer containing 10 mM $MgCl_2$, 11.2 mM β-mercaptoethanol, 0.0015% IGEPAL® CA-630 and 40 μM 4-Methylumbelliferyl β-D-Galactopyranoside (MUG) in PBS is added and the plate is incubated at room temperature for 3 hours. Finally, the β-galactosidase activity is measured using the FLUOstar OPTIMA (BMG LABTECH Gmbh, 30 Offenburg, Germany). Results are expressed as mean±SEM. *P<0.05, P<0.01, *P<0.001 (unpaired student t test).

Tumor Challenge and Treatment

C57Bl/6J female mice are obtained from Harlan Laboratories Ltd, Switzerland. 7 week-old mice are injected subcutaneously into the right flank with $1.10^5$ MCA205 sarcoma or B16F10 melanoma cells or $1.5.10^5$ MCA205 globin-SL8-intron or B16F10 globin-SL8-intron cells. Sarcoma cells are injected in 100 μL sterile PBS while melanoma cells are injected in 50:50 PBS:Matrigel to prevent tumor cell dissemination. Madra.HCl is injected 4, 7, 10 and 14 days post tumor inoculation, in 100 μL $H_2O$+300% (2-Hydroxypropyl)-β-cyclodextrin (w/v). In the same manner EYP59 (compound 7) is injected 4, 7, 10 and 14 days post tumor inoculation, in 100 μL $H_2O$. Area of the tumor is recorded every 3 to 4 days until the tumor reaches the ethical end points. All animal experiments were carried out in compliance with French and European laws and regulations. Results are expressed as mean±SEM. *p<0.05, P<0.01, *P<0.001 (ANOVA with Tukey's multiple comparison test comparing all groups).

Results

Madrasin Treatment Increases Antigenic Presentation of PTP-Derived Antigens in Cancer Cells.

In recent studies inventors have shown that PTPs is a major source of peptides for the endogenous MHC class I pathway in vitro. In order to modulate the presentation PTPs-derived antigens at cancer cells surface, inventors tested the impact of Madrasin treatment on mice tumor cell lines, one melanoma (B16F10) and one sarcoma (MCA205) cell lines. Both murine cell lines were transiently expressing the PTPs-SL8 epitope derived from an intron within the β-Globin gene construct or were kept untransfected. The Madrasin elicits an increase in the PTPs-dependent antigen presentation, with a dose dependent effect in both mouse cell lines (FIG. 1A). These results show that production and presentation of PTPs-derived antigens can be positively modulated in cancer cell lines upon Madrasin treatment. They support the hypothesis that this molecule could be used as positive immunomodulator to potentiate a specific antitumoral immune response dependent on the PTPs production and presentation.

Synthesized Madrasin Hydrochloride (Madra.HCl) Treatment Increases Antigenic Presentation of PTP-Derived Antigen In Vitro and Slow Down Tumor Growth In Vivo.

The above results demonstrate that the Madrasin is able to increase the production and presentation in vitro of PTPs-dependent antigen encoded by intron sequences at the cell surface of treated tumor cell lines. The next question was to see if the Madrasin, which can be only dissolved in DMSO, can have the same effect on tumor growth and CD8$^+$ T cell proliferation in vivo. Unfortunately, inventors were not able to perform an in vivo experiment with Madrasin because of its weak concentration in DMSO. As this first result was encouraging, they decided to generate derivatives of the Madrasin in order to increase cancer immune responses. In fact, Madrasin is insoluble in water and can only be dissolved in DMSO solvent rendering its pharmacokinetic in mice less efficient.

In order to make Madrasin available for broader in vitro and in vivo validation without the use of toxic carriers or cosolvents (DMSO), it was considered necessary to find a strategy to synthesize Madrasin and some derivatives to enhance their solubility and immunomodulator activities.

To this end phosphate prodrugs for example can typically display excellent water solubility, chemical stability, and rapid bioconversion back to the parent drug by phosphatases. The formation of phosphate prodrugs has been applied to increase the aqueous solubility of a variety of molecules, including antineoplastic phenolic natural products and their derivatives, exemplified by combretastatin A-4.

In view to test the news compounds as positive immunomodulator against tumor cell lines, inventors first decided to test them in an in vitro assay. As expected, the new compound, herein identified as "Madra.HCl" was able to be dissolved in water. After treatment of both murine cell lines MCA205 or B16F10 transiently expressing PTPs-SL8 epitope derived from an intron in the β-Globin gene (Globin-intron-SL8) with 5 μM or 10 μM of Madra.HCl, inventors observed an increase in PTPs-dependent antigen presentation in a dose dependent manner (FIG. 1B). $1.10^5$ MCA205 sarcoma cells stably expressing the SIINFEKL (SL8; SEQ ID NO: 1) epitope from an intron in the β-Globin gene (Globin-intron-SL8) were subcutaneously inoculated in mice. Four days after this inoculation, the mice were intraperitoneally vaccinated with a define dose of Madra.HCl. Then every 3 days 20 or 40 mg/kg of Madra.HCl were injected. During that time the tumor growth was monitored every two to three days (FIG. 1C). Inventors observed a significant 50% reduction of tumor growth at day 27 after challenge in mice treated with 20 mg/kg of Madra.HCl (FIG. 1D) and a further 60 to 70% decrease of tumor growth at day 27 after challenge in mice treated with 40 mg/kg of Madra.HCl (FIG. 1D). The same experiment is performed on B16F10 tumor cells expressing the Globin-intron-SL8 construct.

In the same manner, $1\times10^5$ untransfected MCA sarcoma cells were subcutaneously inoculated in mice. Four days after this inoculation, the mice were intraperitoneally vaccinated with a define dose of Madra.HCl. Then, every 3 days the same doses were again injected. During that time the tumor growth was monitored every two to three days (FIG. 1E). Inventors observed a significant 40% reduction of tumor growth at day 21 after challenge in mice treated with 20 mg/kg or 40 mg/kg of Madra.HCl (FIG. 1F).

Furthermore, Madra.HCl treatment was shown to extend survival of mice, with around 25% of survivors 120 days after tumor inoculation when mice were treated with 40 mg/kg of Madra.HCl and with around 15% of survivors 120 days after tumor inoculation when mice were treated with 20 mg/kg of Madra.HCl (FIG. 1G).

Finally, mice which were inoculated with MCA205 tumor cells expressing the Globin-intron-SL8 construct, and that experienced complete tumor regression after treatment with Madra.HCl as described above were re-challenged 100 days later with MCA205 tumor cells expressing the Globin-intron-SL8 construct on the right flank and with B16F10 tumor cells on the left flank. While B16F10 tumors grew over time, the MCA205 tumor cells did not grow in mice (FIG. 1H). These results demonstrate that mice developed a long term anti-tumoral response specific to MCA205 tumor after Madra.HCl treatment.

Madrasin Derivatives Efficiently Increase MHC Class I Presentation of Intron-Derived Antigen In Vitro.

In order to improve the immunomodulatory activity of the Madra.HCl for broader in vitro and in vivo validation without the use of toxic carriers or cosolvents (DMSO), it was considered necessary to find a strategy to change its structure by steal keeping its activity. The next compounds of the present invention were prepared as herein above described.

In order to test the new compounds as positive immunomodulators against tumor cell lines, inventors first decided to test them in an in vitro assay. As expected, few derivatives of Madra.HCl were soluble in water and some other not. Using an MTT test, they identified the IC25 and the IC50 for each compounds in MCA sarcoma and B16F10 melanoma cell lines (FIG. 2). For the rest of the experiments, they decided to treat both cell lines with the IC50 of each compound soluble or not in water. For that purpose, both murine tumor cell lines, transiently expressing PTPs-SL8 epitope derived from an intron in the β-Globin gene (Globin-intron-SL8), were treated O/N with each compounds. Four different observations for the immunomodulatory activity of each compound were made:

The first was that, they noticed an increase in PTPs-dependent antigen presentation with some of the compounds in both murine tumor cell lines (FIG. 3). They could see an increase of the PTP-SL8 presentation after treatment of the murine cell lines with EYP59 (compound 7) (A), EYP201 (compound 6) (B), EYP165 (compound 57) (C) and EYP281 (compound 32) (D) respectively.

The second observation was that some compounds were able to positively increase presentation of their PTPs-derived antigen in only MCA cell lines transiently expressing PTPs-SL8 epitope derived from an intron in the β-Globin gene (FIG. 4). They could see an increase of the PTP-SL8 presentation after treatment of the murine sarcoma cell lines with EYP188 (compound 42) (A) and EYP86 (compound 10) (B) respectively.

Furthermore, the third observation was that some compounds were able to positively increase presentation of our PTPs-derived antigen in only B16F10 cell lines transiently expressing PTPs-SL8 epitope derived from an intron in the β-Globin gene (FIG. 5). Inventors could see an increase of the PTP-SL8 presentation after treatment of the murine melanoma cell lines with EYP174 (compound 41) (A), EYP179 (compound 50) (B), EYP190 (compound 54) (C) and EYP181 (compound 49) (D) respectively.

And finally, the fourth observation was that some compounds were not able to positively increase the presentation of our PTPs-derived antigen in both murine cell lines tested (FIG. 6). Inventors could not see any increase of the PTP-SL8 presentation after treatment of both murine cell lines with EYP177 (compound 46) (A), EYP156 (compound 43) (B), EYP113 (compound 11) (C), and EYP102 (compound 9) (D) respectively.

Madrasin Derivative EYP59 (Compound 7) Efficiently Reduces Tumor Growth In Vivo in an Immune-Dependent Manner.

$1\times10^5$ MCA205 sarcoma cells stably expressing the SIINFEKL (SL8; SEQ ID NO: 1) epitope from an intron in the β-Globin gene (Globin-intron-SL8) were subcutaneously inoculated in mice. Four days after this inoculation, the mice were intraperitoneally vaccinated with a define dose of EYP59. Then, every 3 days, 20 mg/kg were injected. During that time the tumor growth was monitored every two to three days (FIG. 7A). Inventors observed a significant 85% reduction of tumor growth at day 23 after challenge in mice treated with 20 mg/kg of EYP59 (FIG. 7B). In the same manner, $1\times10^5$ untransfected MCA205 sarcoma cells were subcutaneously inoculated in mice. Four days after this inoculation, the mice were intraperitoneally vaccinated with a define dose of EYP59. Then, every 3 days the same doses were again injected. During that time, the tumor growth was monitored every two to three days. Inventors observed a significant 70% reduction of tumor growth at day 19 after challenge in mice treated with 20 mg/kg of EYP59 (FIG. 7C).

In order to assess the requirement of the immune response for this effect, inventors tested the impact of 20 mg/kg EYP59 treatment in immunodeficient nu/nu mice with the same settings as previously described and observed that it has no effect on the tumor growth (FIG. 7D). These results show that tumor size reduction upon EYP59 treatment requires the presence of an active immune response in vivo.

Madrasin Derivative EYP59 (Compound 7) Efficiently Reduces Tumor Growth In Vivo when Injected in Intratumoral or Intravenous Ways.

$1 \times 10^5$ wild type MCA205 sarcoma cells were subcutaneously inoculated in mouse. Four days after this inoculation, the mice were injected with a define dose of EYP59 intratumorally (2.5 mg/kg) or intravenously (5 mg/kg). Then, every 3 days, the same amount of product was injected respectively of the way of administration. During that time the tumor growth was monitored every two to three days. Inventors observed a significant 75% reduction of tumor growth at day 21 after challenge in mice treated intratumorally with 2.5 mg/kg of EYP59 (FIG. 8A). Furthermore, Inventors observed a significant 80% reduction of tumor growth at day 25 after challenge in mice treated intravenously with 5 mg/kg of EYP59 (FIG. 8B).

Discussion

The present invention reveals that specific spliceosome inhibitors have a positive effect on the antitumor immune response and therefore on tumor growth. Splicing abnormalities have emerged as a specific feature of cancer and are studied as predictive markers for patient survival as well as targets for cancer treatments with splicing inhibitors, some of which are currently in development in acute myeloid leukemia. In the present invention inventors demonstrate that some specific derivatives of Madrasin are potent stimulators of the anti-tumor immune response in vitro in sarcoma and melanoma tumor cell lines. They also demonstrate that some Madrasin derivatives are specifically increasing the PTP-dependent antigen presentation in sarcoma cancer model and that some others, different from the first set, are also capable to increase the PTP-dependent antigen presentation in melanoma cancer model. They open the way to new applications within the framework of targeted molecular therapies by highlighting original biomolecular profiles.

The PTPs model describes the pre-spliced mRNA as the template for PTP by an alternative translational event occurring in the nucleus. In the study describing this alternative translation, inventors demonstrated that forced nuclear retention of the mRNA encoding the intronic SL8 peptide leads to an increase in the SL8 antigen presentation. Besides, pladienolides and spliceostatin A (SSA) have been shown to inhibit the splicing by targeting the SF3b, a subcomplex of the U2 small nuclear ribonucleoprotein (snRNP) in the spliceosome, and have been described to promote pre-RNA accumulation in the nucleus. The Madrasin inhibits differently the splicing by preventing stable U4/U6/U5 tri-snRNPs recruitment right after the U2 snRNP fixation. However, it is likely that it also induces pre-mRNA accumulation in the nucleus, resulting in the increase in antigen presentation. The link between pre-mRNA nuclear accumulation and increased antigen presentation is not known. It is tempting to hypothesize that pre-mRNA accumulation in the nucleus provides more templates for PTP production leading to the enrichment of SL8-containing PTPs, used as a major source for SL8 direct presentation.

Furthermore, pre-mRNA splicing is an essential mechanism required for the normal function of all mammalian cells. In the last few years, several studies reported the presence of mutations and overexpression of main spliceosome factors associated with aberrant splicing activity in various cancers. Few years ago, inventors have also provided some evidence that the inhibition of the spliceosome increases MHC class I PTPs-dependent antigen presentation. These findings put the focus on the spliceosome as a potential target in anti-cancer treatment.

As already mentioned, few small molecules have already been reported to inhibit the spliceosome and specifically to inhibit the spliceosome factor SF3B1 function. Although the precise mechanisms of these small molecules are not yet completely understood, it has been reported that they can be effective in cancer therapy by reducing tumor size from 40 to 80% depending of the compound used. The only one to date that has been tested in human is the E7107. It has been stopped because of problems of toxicity. This compound is known to inhibit the spliceosome by interacting with SF3B1.

Moreover, Cytotoxic T lymphocytes failure to reject tumors can in part be explained by an initial inappropriate CTL activation by pAPCs. A defined subset of dendritic cells (DCs) has been described in the tumor microenvironment (TME) to be able to migrate to the tumor draining lymph nodes, deliver intact antigens encountered in the TME and prime directly or not naïve $CD8^+$ T cells. In addition, it was suggested that some DCs are able to directly prime naïve CD8 T cells in the TME. Inventors recently demonstrated that tumor-associated PTPs are a source material for $CD8^+$ T cells cross-priming by DCs and may mainly be transferred from tumor cells to DCs by PTPs-carrying exosomes. Besides, they provided hints that PTPs for endogenous and cross-presentation are produced by the same translation event and that the two pathways then diverge quickly. PTPs are rare products and the efficiency of PTPs vaccines or exosome-containing PTPs vaccines was shown to rely on the previous PTPs enrichment of PTPs proteasome inhibitor. Inventors believe that the splicing inhibitor Madrasin and its different derivatives, in addition to provide more source materials for the direct antigen presentation, enriches the pool of SL8-containing PTPs that serve as a source material for intratumoral DC uptake and cross-presentation, inducing an enhanced SL8-specific $CD8^+$ T cell proliferation.

In the present description, inventors provide both in vitro and in vivo evidences that by modulating the spliceosome activity using specific derivative compounds from Madrasin, it is possible to induce a specific anti-tumor immune response against different cancer models. Madrasin has been reported to interfere in the early step of assembly of the spliceosome. In fact, it has been demonstrated that Madrasin inhibits the A complex of the pre-spliceosome to form a larger pre-catalytic spliceosome B complex. We demonstrated that by inhibiting the formation of the spliceosome, as early as possible using derivatives of the Madrasin in vitro and in vivo, the anti-tumor antigenic presentation was increased significantly, by inducing specifically $CD8^+$ T cell proliferations against PTPs-dependent epitopes. They report that these derivatives can be used as chemotherapeutic agents against melanoma and sarcoma.

REFERENCES

Apcher, S. et al. Major source of antigenic peptides for the MHC class I pathway is produced during the pioneer round of mRNA translation. *Proc. Natl. Acad. Sci. U.S.A.* 108, 11572-7 (2011).

Burg, S. H. et al. Vaccines for established cancer: overcoming the challenges posed by immune evasion. *Nat. Publ. Gr.* 16, 219-233 (2016).

Caron, E. et al. The MHC I immunopeptidome conveys to the cell surface an integrative view of cellular regulation. *Mol Syst Biol.* 7, 533 (2011).

Duvallet, E., et al. Exosome-driven transfer of tumor-associated Pioneer Translation Products (TA-PTPs) for the MHC class I cross-presentation pathway. *Oncoimmunology* 5, e1198865 (2016).

Kmieciak, M., et al. HER-2/neu antigen loss and relapse of mammary carcinoma are actively induced by T cell-mediated anti-tumor immune responses. *Eur. J. Immunol.* 37, 675-685 (2007).

Lee, S. & Sin, J. MC32 tumor cells acquire Ag-specific CTL resistance through the loss of CEA in a colon cancer model. *Hum Vaccin Immunother* 11, 2012-2020 (2015).

Leone, P. et al. MHC class I antigen processing and presenting machinery: organization, function, and defects in tumor cells. *J. Natl. Cancer Inst.* 105, 1172-87 (2013).

Liu, Y. et al. Expression of antigen processing and presenting molecules in brain metastasis of breast cancer. *Cancer Immunol. Immunother.* 61, 789-801 (2012).

Mellman, I., et al. Cancer immunotherapy comes of age. *Nature* 480, 480-489 (2014).

Watson, N. F. S. et al. Immunosurveillance is active in colorectal cancer as downregulation but not complete loss of MHC class I expression correlates with a poor prognosis. *Int. J. Cancer* 118, 6-10 (2006).

Yewdell, J W., et al. Defective ribosomal products (DRiPs): a major source of antigenic peptides for MHC class I molecules? *J Immunol* 157(5):1823-6 (1996).

The invention claimed is:

1. A composition comprising a compound and a pharmaceutically acceptable carrier, optionally together with at least one anticancer agent, the compound being selected from the group consisting of:

5,6-Dimethyl-2-((4-methyl-7-(2-morpholinoethoxy)quinazolin-2-yl)amino)pyrimidin-4(3H)-one

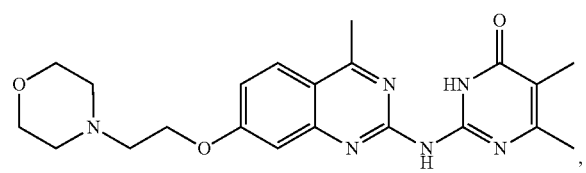

(II)

Sodium 2-((4,5-dimethyl-6-oxo-1,6-dihydropyrimidin-2-yl)amino)-4-methylquinazolin-7-yl phosphate

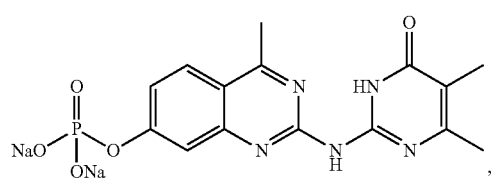

(III)

and

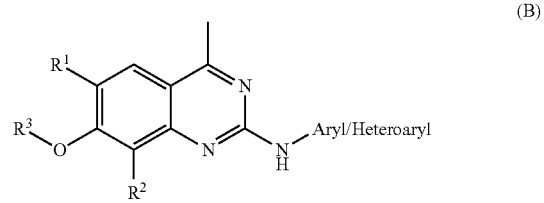

(B)

wherein:

$R^1$ and $R^2$ are independently selected from H, $CH_3$ (Methyl), Cl (Chlorine), and a thiosugar, and $R_3$ is

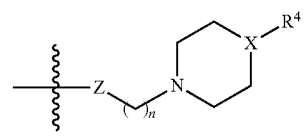

wherein:

$R^4$ is absent, H, $CH_3$ (Methyl), $C_2H_5$ (Ethyl) or n-Propyl,
Z is $CH_2$ or C=O,
n is 1, 2 or 3, and
X is O, N or CH.

2. The composition according to claim 1, wherein:
the compound is 5,6-Dimethyl-2-((4-methyl-7-(2-morpholinoethoxy)quinazolin-2-yl)amino)pyrimidin-4(3H)-one

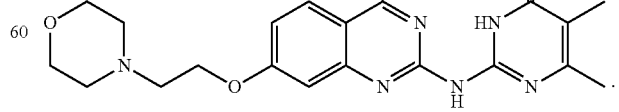

(II)

3. The composition according to claim 1, wherein the compound is sodium 2-((4,5-dimethyl-6-oxo-1,6-dihydropyrimidin-2-yl)amino)-4-methylquinazolin-7-yl phosphate (III)

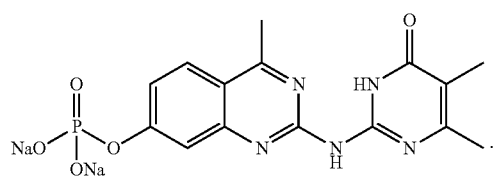

4. The composition according to claim 1, wherein the compound is

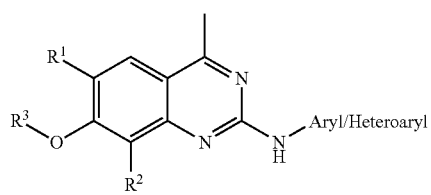

(B)

wherein:

R¹ and R² are independently selected from H, CH₃ (Methyl), Cl (Chlorine), and a thiosugar, and R³ is

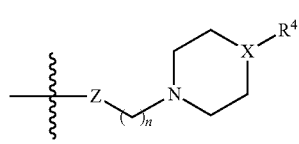

wherein:

R⁴ is absent, H, CH₃ (Methyl), C₂H₅ (Ethyl) or n-Propyl,

Z is CH₂ or C=O, n is 1, 2 or 3, and

X is O, N or CH.

5. A kit comprising a compound and at least one anticancer agent in distinct containers, wherein the compound is selected from the group consisting of:

5,6-Dimethyl-2-((4-methyl-7-(2-morpholinoethoxy)quinazolin-2-yl)amino)pyrimidin-4(3H)-one

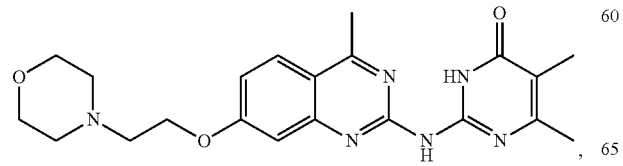

(II)

Sodium 2-((4,5-dimethyl-6-oxo-1,6-dihydropyrimidin-2-yl)amino)-4-methylquinazolin-7-yl phosphate (III)

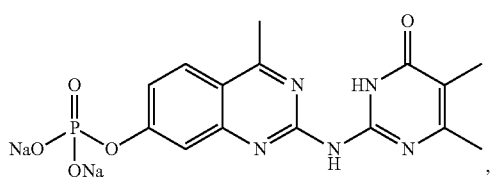

and (B)

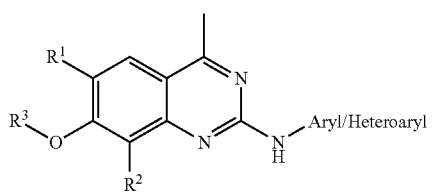

wherein:

R¹ and R² are independently selected from H, CH₃ (Methyl), Cl (Chlorine), and a thiosugar, and R³ is

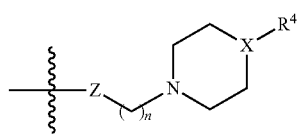

wherein:

R⁴ is absent, H, CH₃ (Methyl), C₂H₅ (Ethyl) or n-Propyl,

Z is CH₂ or C=O, n is 1, 2 or 3, and

X is O, N or CH.

6. A method for treating a carcinoma, sarcoma or blastoma in a subject by ameliorating the disease state of the subject, wherein the method comprises administering a subject in need thereof with a compound selected from:

5,6-Dimethyl-2-((4-methyl-7-(2-morpholinoethoxy)quinazolin-2-yl)amino)pyrimidin-4(3H)-one

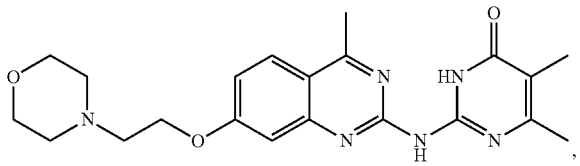

(II)

Sodium 2-((4,5-dimethyl-6-oxo-1,6-dihydropyrimidin-2-yl)amino)-4-methylquinazolin-7-yl phosphate (III)

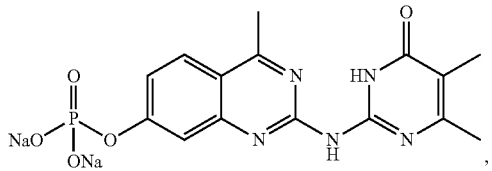

and (B)

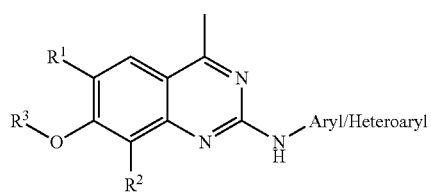

wherein:
R¹ and R² are independently selected from H, CH₃ (Methyl), Cl (Chlorine), and a thiosugar, and
R³ is

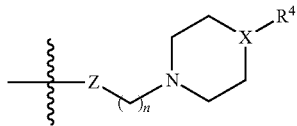

wherein:
R⁴ is absent, H, CH₃ (Methyl), C₂H₅ (Ethyl) or n-Propyl,
Z is CH₂ or C=O,
n is 1, 2 or 3, and
X is O, N or CH.

7. The method according to claim 6, wherein the compound is used in combination with at least one anticancer agent and/or with radiotherapy.

8. The method according to claim 7, wherein the at least one anticancer agent is selected from a chemotherapeutic agent, an immune checkpoint blocker and an anti-cancer vaccine.

9. The method according to claim 6, wherein the compound is selected from the compound of formula II or III, and the cancer is a sarcoma.

10. The method according to claim 6, wherein the compound is the compound of formula II and the carcinoma is a melanoma.

11. The method according to claim 6, wherein the compound stimulates an anti-cancer immune response in the subject.

12. The method according to claim 6, wherein the compound induces or increases the presentation or the production and presentation of Pioneer Translation Products (PTPs)-derived antigens by cancer cells, or changes the immunopeptidome, in the subject.

13. The method according to claim 6, wherein the subject is a mammal.

14. The method according to claim 13, wherein the mammal is a human being.

15. The method according to claim 6, wherein the compound is the compound of formula III, and the cancer is a blastoma.

\* \* \* \* \*

SEQUENCE LISTING

```
<160> NUMBER OF SEQ ID NOS: 1

<210> SEQ ID NO 1
<211> LENGTH: 8
<212> TYPE: PRT
<213> ORGANISM: Artificial Sequence
<220> FEATURE:
<223> OTHER INFORMATION: Epitope

<400> SEQUENCE: 1

Ser Ile Ile Asn Phe Glu Lys Leu
1               5
```